United States Patent
Lawrence et al.

(10) Patent No.: US 9,700,611 B2
(45) Date of Patent: *Jul. 11, 2017

(54) LIVE ATTENUATED CATFISH VACCINE AND METHOD OF MAKING

(71) Applicant: Mississippi State University, Mississippi State, MS (US)

(72) Inventors: Mark L. Lawrence, Starkville, MS (US); Attila Karsi, Starkville, MS (US)

(73) Assignee: MISSISSIPPI STATE UNIVERSITY, Starkville, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,367

(22) Filed: Jun. 2, 2016

(65) Prior Publication Data

US 2016/0339093 A1  Nov. 24, 2016

Related U.S. Application Data

(60) Continuation-in-part of application No. 13/940,125, filed on Jul. 11, 2013, now Pat. No. 9,375,467, which is a division of application No. 12/490,207, filed on Jun. 23, 2009, now Pat. No. 8,507,278.

(60) Provisional application No. 61/074,813, filed on Jun. 23, 2008.

(51) Int. Cl.
| | |
|---|---|
| A61K 39/02 | (2006.01) |
| C12N 1/20 | (2006.01) |
| C12N 1/36 | (2006.01) |
| C12N 9/02 | (2006.01) |
| C12N 9/04 | (2006.01) |
| C12N 9/10 | (2006.01) |
| C12N 9/06 | (2006.01) |
| C12N 15/10 | (2006.01) |
| C12Q 1/02 | (2006.01) |
| C12Q 1/66 | (2006.01) |
| A61K 39/00 | (2006.01) |

(52) U.S. Cl.
CPC .............. *A61K 39/025* (2013.01); *C12N 1/20* (2013.01); *C12N 1/36* (2013.01); *C12N 9/001* (2013.01); *C12N 9/0006* (2013.01); *C12N 9/0014* (2013.01); *C12N 9/0051* (2013.01); *C12N 9/1014* (2013.01); *C12N 15/102* (2013.01); *C12Q 1/025* (2013.01); *C12Q 1/66* (2013.01); *C12Y 101/01037* (2013.01); *C12Y 103/00* (2013.01); *C12Y 103/05001* (2013.01); *C12Y 104/04002* (2013.01); *C12Y 108/01004* (2013.01); *C12Y 201/0201* (2013.01); *A61K 2039/522* (2013.01); *A61K 2039/552* (2013.01)

(58) Field of Classification Search
None
See application file for complete search history.

(56) References Cited

PUBLICATIONS

Mercado-Lubo (Infect. Immun., 76:1128-1134; 2008).
Yimga et al. (Infect. Immun., 74: 1130-1140).
Karsi et al. (Appl. Environ. Microbiol., 75: 2166-2175, 2009).
Ellis, R.W. (Chapter 29 of "Vaccines" [Plotkin, S.A. et al. (eds) published by W.B. Saunders Company (Philadelphia) in 1988, p. 568-575.
Belas et al. (J. Bacteriol)., 158: 890-896, 1984).
Lawrence et al. (J. Aquatic Animal Health, 13: 291-299, 2001).
Karsi et al. (Plasmid, 57: 286-295, 2007).
Courtright and Henning (Courtright et al., J. Bacteriol., 102:722-728, 1970).

*Primary Examiner* — Brian J Gangle
(74) *Attorney, Agent, or Firm* — Butler Snow LLP

(57) ABSTRACT

Live attenuated bacteria vaccines against enteric septicemia of fish, especially catfish, and methods related to the same. Mutant strains of the bacteria *Edwardsiella ictaluri* (a pathogenic bacterial strain of *Enterobacteriaceae*) are provided. The mutant *Edwardsiella ictaluri* bacteria (or other pathogenic bacterial strain of *Enterobacteriaceae*) contain one or more gene deletions or disruptions that result in less virulent bacterial strains as live attenuated vaccine compositions against virulent wild-type *Edwardsiella ictaluri* bacteria (or other pathogenic bacterial strain of *Enterobacteriaceae*). The mutant strains showing the best immunological protection and safety as a vaccine are the triple mutants ESC-NDKL1 (ΔgcvPΔsdhCΔfrdA) strain and ESC-NDKL2 (ΔgcvPΔsdhCΔmdh) strain, with the ESC-NDKL1 strain providing the greatest safety and efficacy of these two triple mutants.

20 Claims, 10 Drawing Sheets

LIVE ATTENUATED CATFISH VACCINE AND METHOD OF MAKING

CROSS-REFERENCE TO RELATED APPLICATIONS

This application is a continuation-in-part of U.S. application Ser. No. 13/940,125 to Mark L. Lawrence and Attila Karsi filed on Jul. 11, 2013, now issued as U.S. Pat. No. 9,375,467, which is a division of U.S. application Ser. No. 12/490,207 to Mark L. Lawrence and Attila Karsi filed on Jun. 23, 2009, now issued as U.S. Pat. No. 8,507,278, which claims priority to U.S. Provisional Application No. 61/074,813 filed on Jun. 23, 2008, the contents of each of the foregoing are incorporated herein by reference in their entirety.

FEDERALLY SPONSORED RESEARCH

This invention was made with government support under 2004-35204-14211, 2009-65119-05671 and 2014-70007-22359 awarded by the National Institute of Food and Agriculture, USDA. The government has certain rights in the invention.

FIELD OF THE INVENTION

The present invention is generally directed toward a live attenuated vaccine for fish, and more particularly, it is directed toward mutant strains of *Edwardsiella ictaluri* as a live attenuated vaccine against enteric septicemia of catfish and methods related to the same.

BACKGROUND OF THE INVENTION

Channel catfish farming is the largest contributor to U.S. aquacultural production. In 2015, catfish growers in the US produced more than $361 million worth of catfish, of which $201 million (55.7%) was from Mississippi (www.nass.usda.gov). Catfish farmers reported 37% mortality rate (U.S. Department of Agriculture, 2011) due to enteric septicemia of catfish (ESC). *Edwardsiella ictaluri* (also referred to herein as *E. ictaluri*) is the causative agent of enteric septicemia of catfish. Like some other species in the *Enterobacteriaceae, E. ictaluri* has the ability to resist killing by professional phagocytes. In particular, *E. ictaluri* is resistant to channel catfish neutrophils, which is an important aspect of pathogenesis because (1) neutrophils are the predominant cell type in channel catfish intestinal tract immune cells, and (2) the intestine is an important site of entry for *E. ictaluri*. *E. ictaluri* is also resistant to killing by the alternative complement pathway in channel catfish. Although a commercial live attenuated vaccine is now available and antibiotics are still used against *E. ictaluri* and ESC, ESC is still a major threat to the catfish industry (Klesius and Shoemaker, 1999). Live attenuated vaccines often offer the best prospect for vaccines by providing good protection against diseases through stimulating cellular immune responses (Id.), but the currently available commercial vaccine leaves much to be desired in performance and safety.

The tri-carboxylic acid (TCA) cycle supplies intermediates and ATP for bacterial biosynthesis, thus transcription of genes encoding the enzymes of the TCA cycle is regulated by the availability of amino acids (Somerville et al., 2003). The TCA cycle exerts a metabolic regulation over the synthesis of capsular polysaccharide by gluconeogenesis (Sadykov et al., 2010). Previous research into the role of the metabolic pathway in pathogenic bacteria, such as in *Escherichia coli*, has demonstrated that succinate dehydrogenase and fumarate reductase as part of the TCA cycle are related membrane-bound enzyme complexes (Cecchini et al., 2002). It has been shown that *Salmonella enterica* serovar *Typhimurium* requires glycolysis and glucose for intracellular replication in macrophage, and the complete TCA cycle is needed for full virulence in the murine infection model (Yimga et al., 2006).

In *E. ictaluri*, some live attenuated vaccine candidates have been developed, including auxotrophic (Lawrence et al., 1997; Thune et al., 1999) and iron-siderophore uptake (Abdelhamed et al., 2013) mutants. Also, we reported that TCA and one-carbon (C1) metabolism pathways contribute to *E. ictaluri* pathogenesis (Dahal et al., 2014; Dahal et al., 2013). In particular, some TCA and C1 metabolism mutants provided good protection against wild-type *E. ictaluri* infections in fingerling, which was not the case when tested in catfish fry (14-day old). Thus, there is still a need for a live attenuated bacterial vaccine against ESC in fish, especially catfish, which has improved safety and protection levels of the TCA and C1 metabolism mutants.

SUMMARY OF THE INVENTION

Now disclosed are compositions for use as live attenuated vaccines and methods related to the same that overcome the stated deficiencies in the prior art, as well as other benefits. The compositions comprise mutant strains of the bacteria *Edwardsiella ictaluri* or another pathogenic bacterial strain of *Enterobacteriaceae*. Preferably, the mutant strains are the triple mutants ESC-NDKL1 (ΔgcvPΔsdhCΔfrdA) and ESC-NDKL2 (ΔgcvPΔsdhCΔmdh) in the bacteria *Edwardsiella ictaluri* or another pathogenic bacterial strain of *Enterobacteriaceae*. More preferably, the mutant strain is the ESC-NDKL1 strain in the bacteria *Edwardsiella ictaluri*.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements to the several drawings as follows:

FIG. 1 depicts an overview of mutant screening procedures using BLMS method.

FIG. 2 depicts the results of a vaccine efficacy trial and shows the percent mortalities resulting from vaccination using mutants developed through the BLMS method. Percent mortalities are the mean of four replicate tanks per treatment. PBS is saline control, Wt ("wild-type") is parent strain 93-146, and AQUAVAC-ESC is a commercially available live attenuated vaccine. Capital letters above each bar indicate statistical groupings. Groups marked with the same capital letter do not show statistically significant differences. ($P<0.05$)

FIG. 3 depicts the results of percent mortalities resulting from challenge with parent strain 93-146 twenty one days post-vaccination using mutants developed through the BLMS method. As in FIG. 2, percent mortalities are the mean of four replicate tanks per treatment. PBS is saline control, Wt is parent strain 93-146, and AQUAVAC-ESC is a commercially available live attenuated vaccine. Capital letters above each bar indicate statistical groupings. Groups marked with the same capital letter do not show statistically significant differences. (P<0.05)

FIG. 4 is a photograph of an electrophoresis gel confirming the ESC-NKDL1 and ESC-NKDL2 in-frame deletion constructs using PCR. The first lane is 1 Kb Plus marker.

FIGS. 5A and 5B are bar graphs showing percent mortality of catfish fry. FIG. 5A is a bar graph showing percent mortalities of catfish fry immunized with ESC-NKDL1, ESC-NKDL2, AQUAVAC-ESC, and sham control. FIG. 5B is a bar graph showing percent mortalities of catfish fry challenged with wild-type *E. ictaluri* at 21 days post-immunization. (*p<0.05; p<0.01; *p<0.005)

FIGS. 6A and 6B are bar graphs showing percent mortality of catfish fingerlings. FIG. 6A is a bar graph showing percent mortalities of catfish fingerlings immunized with ESC-NKDL1, ESC-NKDL2, AQUAVAC-ESC, and sham control. FIG. 6B is a bar graph showing percent mortalities of efficacy for catfish fingerlings challenged with wild-type *E. ictaluri* at 21 days post-immunization. (*p<0.05; p<0.01; *p<0.005)

FIG. 7A is a bar graph showing the mean number of fish remaining in each pen at harvest. This data represents the mean of four replicate pens in each earthen pond. FIG. 7B is a bar graph showing the probability of survival of each treatment. The data represents the mean of four replicate pens in each earthen pond.

DETAILED DESCRIPTION

Figure 1:
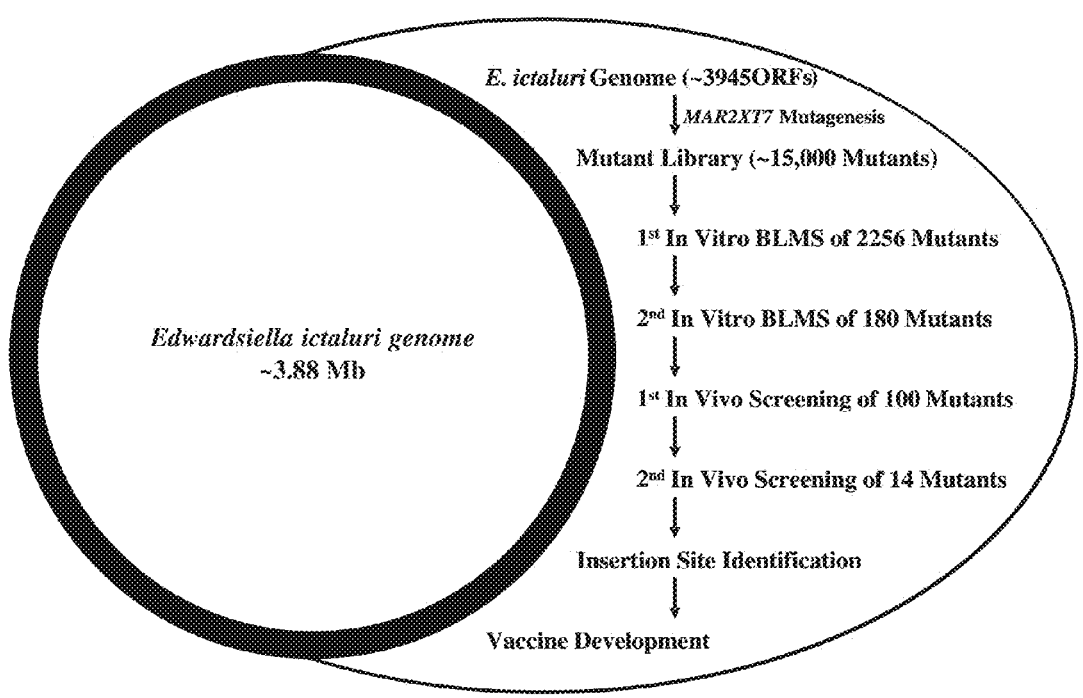

The BLMS method described herein was successfully used in the development of a vaccine for channel catfish against *E. ictaluri*. Although the following embodiment describes the methods as applied in vaccine development against *E. ictaluri*, the BLMS method is widely applicable to the screening of any bacterial species. Other methods were employed below to prepare mutant *E. ictaluri* for development of live attenuated vaccines for channel catfish against *E. ictaluri*. These other methods can be used to create the equivalent mutants in other bacterial species for live attenuated vaccines in channel catfish and in other fish and/or catfish species.

Technological developments in functional genomics allow detection of molecular phenotypes that evade detection at the physiological or morphological levels. We disclose a new high-throughput functional genomics tool that we call bioluminescence mutant screening (BLMS) that translates molecular genotypes (gene mutations) to physiological phenotypes (light production) in bacteria and allows application of forward genetics.

BLMS involves random transposon mutation of a bacterial strain expressing bacterial luciferase operon (luxCDABE) in a stable plasmid. Following this approach, we produced a random *E. ictaluri* mutant library that conditionally expresses luxCDABE genes from a stable plasmid, pAKgfplux2, which allows the tracking of mutants in a pool under different experimental conditions.

In an alternative embodiment, luxCDABE genes could also be incorporated into bacterial chromosomes for a similar BLMS purpose. Chromosomal insertion of luxCDABE operon may require more sensitive instrumentation to alleviate the reduced amount of bioluminescence produced from a single copy lux operon. Our BLMS procedure requires use of IPTG because our mutant library expresses lux operon conditionally from a lacZ promoter on pAKgfplux2, which also carries a $lacI^q$ suppressor gene. To eliminate use of IPTG in bacterial strains without the presence of $lacI^q$ gene in their genome use of a mutant library constitutively expressing lux operon from a stable plasmid, such as pAKlux2 and pAKgfplux1, would be preferred.

Through screening 2,256 mutants from *E. ictaluri* mutant library, we were able to identify 14 attenuated mutants at the end of in vitro BLMS and in vivo fish screening. Eight mutants were common to neutrophil and serum screening while only four and only two mutants were identified as neutrophil and serum mutants, respectively. The fourteen identified *E. ictaluri* mutants were first characterized in terms of their virulence and vaccine potential and later mutated genes in each mutant were determined by transposon insertion sites identification. Finally, selected mutants were compared to a commercial vaccine (AQUAVAC-ESC®) to determine their commercial value. Findings from our research suggest that BLMS is a very powerful screening method for development of live attenuated vaccines. Fourteen mutants identified by utilizing BLMS showed reduced virulence as compared to wild-type *E. ictaluri* and provided increased protection from ESC compared to non-vaccinated controls. Among the 14 mutants, we observed redundant mutations in two genes. Three different mutants harbored transposon insertion at different locations in gcvP, which encodes glycine cleavage system protein P. Two different mutants harbored transposon insertion at the same location in rseB, which encodes a negative regulator of sigma E activity. This provides confirmation that BLMS procedure is a sensitive method detecting true targets.

BLMS can detect novel virulence relevant genes located on native plasmids or show importance of native plasmids in bacterial virulence if random mutation occurs in the origin of replication of native plasmids. While applying BLMS to *E. ictaluri*, we observed that at least one of the two native plasmids of *E. ictaluri* (pEI1) may be important in *E. ictaluri* virulence because two different locations were targeted on this plasmid in two different mutants (EiAKMut04 and EiAKMut10).

Production of *Edwardsiella ictaluri* Mutant Library

A library of random transposon insertion mutations in conditionally bioluminescent *E. ictaluri* strain 93-146 carrying pAKgfplux2 was generated. The library containing approximately 15,000 mutants was created by using a derivative of the mariner transposon Himar1 carried on pMAR2xT7 plasmid. The library consisted of mutants arrayed in 39 384-well plates. A duplicate of the whole library was also prepared. The produced mutant library is compatible with genetic footprinting of the mutants with transposon-site hybridization (TraSH) analysis.

Identification of Serum and Neutrophil Susceptible *Edwardsiella ictaluri* Mutants We used the high throughput bioluminescence mutant screening (BLMS) procedure to identify virulence relevant genes of gram negative bacteria in vitro. We screened 2,256 mutants against both serum and neutrophils using BLMS and identified 180 mutants exhibiting light reduction during incubation with these host factors. A second round screening of these 180 mutants in quadruplicate samples allowed us to identify 35 serum, 39 neutrophil, and 26 both serum and neutrophil susceptible mutants for in vivo studies (100 total mutants for continued study). A general outline of the integrated procedures including in vitro BLMS and in vivo fish screening applied can be seen in FIG. 1. Injection of catfish with 100 BLMS-selected mutants resulted in identification of 14 attenuated mutants including 8 mutants susceptible to both serum and neutrophils, 4 susceptible to neutrophils, and 2 susceptible to serum, which were further characterized in vivo.

Characterization of Virulence and Vaccine Potentials of *Edwardsiella ictaluri* Mutants In vitro BLMS allowed us to reduce the number of target mutants to an amenable size for in vivo characterization. Fish were infected with the 14 mutants, and their attenuation and vaccine potentials were determined (see TABLE 1). Virulence of EiAKMut07 and EiAKMut09 appeared to be higher than other mutants while *E. ictaluri* wild-type was the most virulent in immersion immunization. EiAKMut02, EiAKMut07, EiAKMut10, and EiAKMut12 provided more protection than other mutants. Similarly, EiAKMut07 and EiAKMut09 were also the most virulent strains in the injection immunization though they were attenuated as compared to wild-type strain. Virulence of the second category of mutants in injection immunization ranged from 1.25% to 11.67%, while the third category of mutants including EiAKMut02, EiAKMut03, EiAKMut04, and EiAKMut06 seemed to be non-virulent. After immersion infection, efficacy of EiAKMut02, EiAKMut08, and EiAKMut12 were statistically superior to others.

TABLE 1

Summary of in vivo mutant characterization results

| | Immunization$^{Im}$ | | Wt challenge$^{Im}$ | | Immunization$^{In}$ | | Wt challenge$^{Im}$ | |
|---|---|---|---|---|---|---|---|---|
| Groups | % M | SE | % M | SE | % M | SE | % M | SE |
| EiAKMut01 | — | — | 1.32 | 1.32 | 6.67 | 3.33 | 5.46 | 0.10 |
| EiAKMut02 | — | — | — | — | — | — | — | — |
| EiAKMut03 | — | — | 6.35 | 5.01 | — | — | 1.67 | 1.67 |
| EiAKMut04 | — | — | 2.17 | 2.17 | — | — | 1.67 | 1.67 |
| EiAKMut05 | — | — | 1.09 | 1.09 | 1.67 | 1.67 | 3.33 | 3.33 |
| EiAKMut06 | — | — | 2.39 | 1.38 | — | — | 2.63 | 1.52 |
| EiAKMut07 | 1.19 | 1.19 | — | — | 58.33 | 8.82 | 3.03 | 3.03 |
| EiAKMut08 | — | — | 1.32 | 1.32 | 1.67 | 1.67 | — | — |
| EiAKMut09 | 1.25 | 1.25 | 2.44 | 1.41 | 48.33 | 9.47 | 4.44 | 4.44 |
| EiAKMut10 | — | — | — | — | 11.25 | 1.26 | 4.10 | 2.55 |
| EiAKMut11 | — | — | 22.02 | 8.63 | 1.25 | 1.19 | 2.72 | 1.58 |
| EiAKMut12 | — | — | — | — | 10.00 | 2.04 | — | — |
| EiAKMut13 | — | — | 1.00 | 1.00 | 11.67 | 7.25 | 5.85 | 0.48 |
| EiAKMut14 | — | — | 18.78 | 3.80 | 5.00 | 0.22 | 1.75 | 1.75 |
| EiWt | 17.55 | 8.01 | 1.39 | 1.39 | 83.75 | 3.75 | — | — |
| PBS | — | — | 88.73 | 1.69 | — | — | 12.50 | 2.50 |

Im, immersion;
In, injection;
Wt, wild-type *E. ictaluri* 93-146;
M, mortality;
SE, standard error;
—, no mortality observed.

Identification of MAR2xT7 Insertions in *Edwardsiella ictaluri* Genome

MAR2XT7 insertion locations were determined using single primer PCR amplification of transposon ends and nested primer sequencing. We determined the insertion locations of MAR2XT7 and identified disrupted (non-functional) genes from all fourteen mutants (TABLE 2). Gene identification using database searches indicated that glycine cleavage system protein P (gcvP) was disrupted in three of the mutants (EiAKMut02, EiAKMut03, and EiAKMut08) but at different locations within the genetic sequence. Similarly, negative regulator of sigma E activity (rseB) gene was mutated at the same location in EiAKMut01 and EiAKMut07. Interestingly, two genes located on one of the native plasmids of *E. ictaluri* (pEI1) were also mutated. One of these genes was a putative RNA one modulator protein while the other was a hypothetical protein.

TABLE 2

Summary of insertion identification results

| Mutants | Type | ID | Location |
|---|---|---|---|
| EiAKMut01 | NS | Negative regulator of sigma E activity (rseB) | MAR2XT7^TAttgcggg |
| EiAKMut02 | NS | Glycine cleavage system protein P (gcvP) | MAR2XT7^TAcccgctg |
| EiAKMut03 | NS | Glycine cleavage system protein P (gcvP) | MAR2XT7^TAtatcgct |
| EiAKMut04 | NS | Hypothetical protein pEI1__p1 | M4R2XT7^TAtactctc |
| EiAKMut05 | NS | Succinate dehydrogenase/ fumarate reductase, cytochrome b subunit | MAR2XT7^TAgaatacc |

TABLE 2-continued

Summary of insertion identification results

| Mutants | Type | ID | Location |
|---|---|---|---|
| EiAKMut06 | NS | Electron transport complex protein RnfB | MAR2XT7^TAccggcag |
| EiAKMut07 | NS | Negative regulator of sigma E activity (rseB) | MAR2XT7^TAttgcggg |
| EiAKMut08 | NS | Glycine cleavage system protein P (gcvP) | MAR2XT7^TAgttggcg |
| EiAKMut09 | N | Fimbrial chaperon protein | MAR2XT7^TAccacgct |
| EiAKMut10 | N | Putative RNA one modulator protein pEI1_p4 | MAR2XT7^TAattccca |
| EiAKMut11 | N | 2-oxoglutarate dehydrogenase E1 component | MAR2XT7^TActtgacc |
| EiAKMut12 | N | Malate dehydrogenase | MAR2XT7^TAttcagaa |
| EiAKMut13 | S | UDP-glucose 6-dehydrogenase | MAR2XT7^TAtacctta |
| EiAKMut14 | S | TnpA | MAR2XT7^TAgaagtca |

N, neutrophil sensitive;
S, serum sensitive;
NS, neutrophil and serum sensitive;
MAR2XT7, mariner transposon;
^, insertion point;
TA, two base TA duplication;
lowercase letters, 7 bp flanking unique gene sequences of *E. ictaluri*.

Attenuation and Efficacy of *Edwardsiella ictaluri* Mutants and AQUAVAC-ESC

Figure 2:
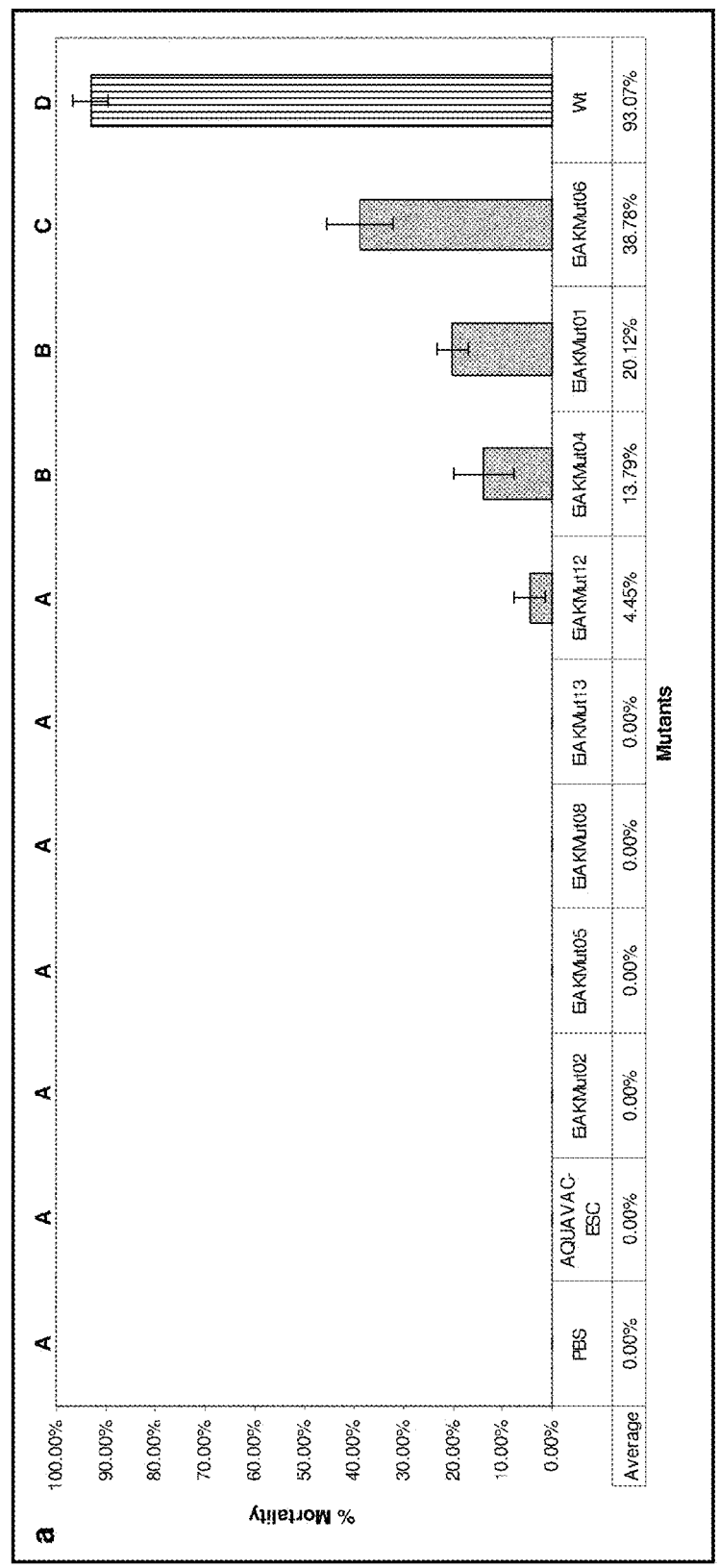
Figure 3:
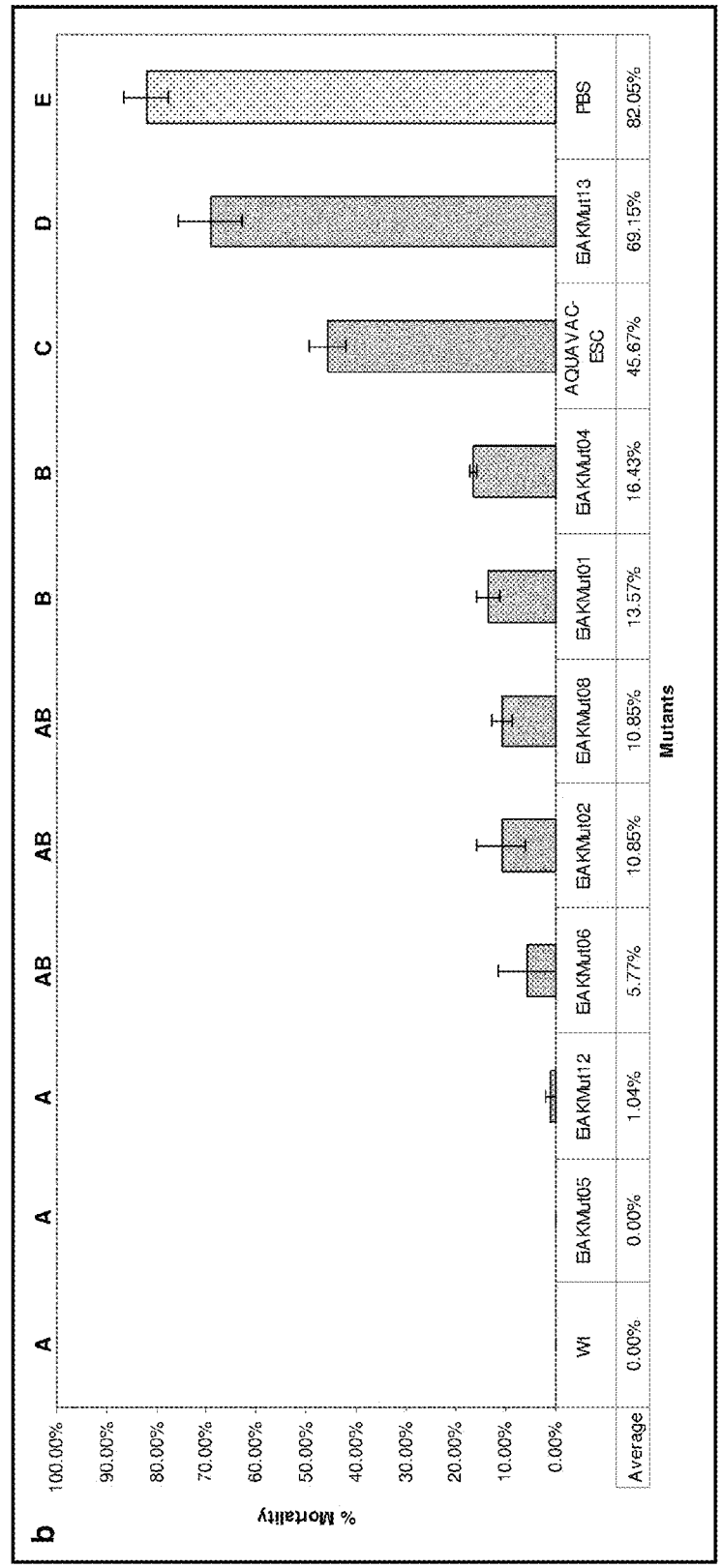

We compared our attenuated *E. ictaluri* mutants with a commercial live attenuated vaccine to determine whether our mutants provide reduced virulence and improved protection against the wild-type *E. ictaluri* infections. As can be seen from FIG. 2 and FIG. 3, attenuation and efficacy experiments indicated that some of our mutants performed better than AQUAVAC-ESC while others did not. Immersion immunization indicated that AQUAVAC-ESC, EiAKMut02, EiAKMut05, EiAKMut08, and EiAKMut13 were completely attenuated while others showed increased attenuation as compared to wild-type *E. ictaluri*. Infection of immunized fish indicated that EiAKMut05 provided the best protection with no mortality in the immunized fish. Six other mutants indicated improved protection as compared to AQUAVAC-ESC. EiAKMut13 performed inferior to commercial vaccine in terms of protection, but EiAKMut13 provided slightly greater protection against wild-type infection as compared to the sham vaccinated fish.

EXAMPLE

Live Attenuated Vaccine for Use in Catfish

The following description more particularly discloses the steps used in practicing the BLMS method as applied to the BLMS *E. ictaluri* live attenuated vaccine.

Bacterial Strains, Plasmids, and Growth Conditions. *Escherichia coli* (*E. coli*) SM10 λpir was used as the donor strain in conjugations for transfer of pAKgfplux2 and pMAR2XT7 into *Edwardsiella ictaluri* strain 93-146. *E. ictaluri* and *E. coli* DH5α carrying pAKgfplux2 were used as negative and positive controls in neutrophil and serum screening experiments. *E. coli* strains were grown using Luria-Bertani (LB) broth and agar plates at 37° C. and *E. ictaluri* was grown using brain heart infusion (BHI) broth and agar plates at 30° C. Antibiotics were added to the following final concentrations: ampicillin (100 g/ml), colistin (12.5 g/ml), gentamicin (12.5 g/ml). 2 mM Isopropyl-β-D-thiogalactopyranoside (IPTG) was used in growth medium and screening assays to induce expression of bacterial luciferase operon (luxCDABE) from the lacZ promoter in pAKgfplux2. *E. ictaluri* minimal medium was used to eliminate auxotrophic mutants.

Construction of *Edwardsiella ictaluri* Mutant Library. MAR2xT7 insertions were generated by introducing pMAR2xT7 from *E. coli* SM10 pir into *E. ictaluri* carrying pAKgfplux2 in conjugal mating as described in Karsi, A. & Lawrence, M. L. Broad host range fluorescence and bioluminescence expression vectors for Gram-negative bacteria. *Plasmid* 57, 286-295 (2007), herein incorporated by reference. Transposants were selected on 20×20 cm LB agar plates containing 12.5 g/ml colistin and 12.5 g/ml gentamicin. Putative transposants were picked robotically using a Flexsys Colony Picker (GENOMIC SOLUTIONS, Ann Arbor, Mich.) into 60 μl of LB broth containing colistin and gentamicin in 384-well microtiter plates and grown overnight in HIGRO shaker (GENOMIC SOLUTIONS) at 30° C. A duplicate library was prepared by the Flexsys Colony Picker before sterile glycerol was robotically added to the cultures at a final concentration of 20%. Plates were sealed with aluminum foil to prevent cross contamination, lids were taped to prevent freeze drying, and libraries were frozen at −80° C.

Catfish Serum and Neutrophil Preparation. Specific pathogen free (SPF) fish facility at the College of Veterinary Medicine, Mississippi State University maintains SPF channel catfish. For serum preparation, 1-2 kg SPF catfish were anesthetized in water containing 200 mg/l tricaine methanesulfonate (MS-222) and blood was collected at 1% of body weight. A recovery period of one month was given for subsequent blood collections. Serum was obtained and stored at −80° C. as single use aliquots. Neutrophils were isolated from the single cell suspensions of anterior kidney cells of SPF catfish (38.63±0.68 cm, 424.20±23.34 g) using discontinuous percoll gradient centrifugation procedure described previously. Purity of neutrophils collected from the 1.060-1.080 interface was determined using flow cytometry.

In Vitro Mutant Screening Using Catfish Serum and Neutrophils. 384-well plates containing the frozen mutants were taken out from the −80° C. and aluminum cover is removed immediately. Plates were centrifuged briefly and returned to 4° C. until the culture thawed completely. Four 96-well plates containing 195 μl of BHI medium with colistin and gentamicin antibiotics and 2 mM IPTG were prepared. Five microliters of mutant bacteria were inoculated in each well and were grown at 30° C. by shaking at 250 RPM for 16-18 hours. The next day, 10 μl of mutant culture containing approximately 106 CFU was mixed with 90 μl of catfish serum containing 2 mM IPTG and plates were returned to the imaging chamber of an IVIS Imaging System 100 Series (XENOGEN CORP., Alameda, Calif.).

Initial bioluminescence of the serum was detected after five minute pre-incubation of samples in the imaging chamber adjusted to 30° C. to eliminate temperature effect on light production. After initial imaging, subsequent images were captured from the same plates at every 15 minute intervals during the 90 minute data collection. Images were analyzed and photons emitted from each well were quantified using Living Image Software v2.50 (XENOGEN CORP.). Percent light change between the first and last measurement times was determined for each mutant and compared to serum resistant (*E. ictaluri* 93-146 pAKgfplux2) and serum sensitive (DH5α pAKgfplux2) controls included in each plate.

Neutrophil screening was accomplished by setting up phagocytosis assays including freshly isolated neutrophils with 75% or higher purity, 15% SPF catfish serum, 2 mM IPTG, and mutant bacteria. Neutrophil to bacteria numbers were adjusted to give a ratio between 1:40 and 1:80. Bioluminescence imaging was conducted as described above in the serum screening procedure. Percent bioluminescence change in 2,256 mutants was calculated and compared to those of positive and negative controls.

One hundred and eighty mutants with reduced bioluminescence were re-screened against serum and neutrophils in quadruplicate samples and data were analyzed using General Linear Model procedure of SAS v 9.1 (SAS Institute Inc., Cary N.C.). 100 mutants were selected for in vivo screening studies.

In Vivo Mutant Screening. SPF channel catfish (5.20±0.18 cm) were transferred from the SPF fish facility to 40 L flow-through tanks with dechlorinated municipal water. Fish were maintained in well-aerated tanks with a water temperature of 28° C. throughout the experiments. After one weak of acclimation, fish were anesthetized in water containing 100 mg/l MS-222 and each mutant was injected into 15 catfish at a concentration of approximately $1 \times 10^7$ CFU in 100 µl phosphate-buffered saline (PBS). Wild-type and PBS injected fish were also included in the experiment as positive and negative controls. Fish were monitored daily and dead fish were removed from the tanks. Percent mortality rates indicated attenuation state of serum, neutrophil, and both serum and neutrophil mutants. Fourteen mutants with the highest attenuation rates were further characterized.

Determination of Virulence and Vaccine Potentials. Virulence and efficacy of the 14 mutants were characterized by infecting catfish by both intraperitoneal injection and immersion. Each 40 liter flow-through tank contained twenty fish, and four tanks were used for each mutant. Fish were allowed to acclimate for one week. Quadruplicate wild-type and PBS controls were also included in all experiments. Bacteria numbers were adjusted to be equal by determining $OD_{600}$ readings and adjusting volumes accordingly. In the first study, fish (13.80±0.26 cm, 25.83±1.49 g) were infected by immersion in water containing $1 \times 10^6$ CFU/ml for one hour. After 21 days, immunized fish were infected with wild-type E. ictaluri by immersion in water with $1 \times 10^7$ CFU/ml for one hour. Fish were monitored and dead fish were removed daily. In the second study, fish (14.61±0.33 cm, 32.70±2.36 g) were anesthetized and infected by injecting $1 \times 10^5$ CFU in 100 µl PBS. After 21 days, fish were infected by immersion as described above. Virulence and efficacy of each mutants and controls were calculated from the fish mortality rates.

Identification of Transposon Insertion Sites. Transposon insertion sites were identified by using a single primer PCR protocol. Mutants were grown for 18 hours and genomic DNA was prepared using WIZARD Genomic DNA Purification Kit (PROMEGA). In the first round of PCR reaction, the transposon specific template was amplified linearly for 40 cycles. A second round produced specific and non-specific amplicons due to low annealing temperature at 30° C. The final round further amplified the amplicons. The 25 µl PCR reaction contained 0.2 mM dNTPs, 0.2 µM transposon specific primer, 1.5 mM MgCl2, buffer, and 1.25 units of Taq polymerase (PROMEGA). The five µl single primer PCR reaction was cleaned with 2 µl of EXOSAP-IT enzyme mix (USB CORP.) according to the manufacturer's instructions. Twenty micoliters of BIGDYE v3.1 sequencing reaction contained 2 µl of EXOSAP-IT enzyme mix treated template and 10 µM nested transposon specific primer. Transposon specific sequences were trimmed and remaining bacterial sequences were searched against nucleotide and protein databases using BLAST program.

Vaccination Studies. Virulence and efficacy of mutants were compared to a commercial vaccine (AQUAVAC-ESC). Experiment contained 10 mutants, a mixed group containing Mut02, Mut04, Mut05, and Mut06, a commercial live attenuated vaccine, and wild-type and sham controls. Two of the mutants (Mut02 and Mut08) harbored transposon insertions in the same gene but at different locations and therefore served as an internal control in the experiments. Each 40 liter flow-through tank contained 25 fish and four tanks were assigned to each group. Fish were allowed to acclimate for two weeks before bacterial challenges. Bacteria numbers were adjusted to be equal by determining $OD_{600}$ readings and adjusting volumes accordingly. For vaccination, fish (11.62±0.16 cm, 15.36±0.65 g) were infected by immersion in water containing $2 \times 10^7$ CFU/ml for one hour. After 21 days, immunized fish were infected with wild-type E. ictaluri by immersion in water with $1 \times 10^7$ CFU/ml for one hour. Fish were monitored and dead fish were removed daily. Mean percent mortalities for each group were calculated, arcsine-transformed, and analyzed using PROC GLM procedure of SAS 9.1 (SAS Institute Inc., Cary, N.C.).

Analysis of the Mutants

Succinate-ubiquinone oxidoreductase (SQR) encoded by the sdhCDAB gene cluster and menaquinol-fumarate oxidoreductase (QFR) encoded by the fJdABCD gene cluster are part of the tri-carboxylic acid (TCA) cycle and are structurally and functionally related membrane-bound enzyme complexes. EiAKMut05 has an insertion in the sdhC gene, which encodes one of four subunits of the succinate dehydrogenase complex. SdhC is one of the two subunits that anchor the complex in the cytoplasmic membrane. Succinate dehydrogenase is part of the aerobic respiratory chain and the Krebs cycle, oxidizing succinate to fumarate while reducing ubiquinone to ubiquinol. It is closely related to fumarate reductase, which catalyzes the reverse reaction. Succinate dehydrogenase and fumarate reductase can replace each other at different relative rates and with different apparent substrate affinities. Because of fumarate reductase's ability to convert succinate to fumarate, sdhCDA mutant of Salmonella enterica serovar Typhimurium were slightly attenuated and complete attenuation was achieved by succinate dehydrogenase/fumarate reductase double mutation. In E. ictaluri, sdhC is the first gene in a polycistronic operon that encodes the four components of succinate dehydrogenase; therefore, it is possible that the mutation in sdhC has a polar effect on expression of downstream genes. Our results indicate that attenuation of E. ictaluri was achieved with sdhC mutation without a need for generating double mutants in frd genes. An explanation for this could be that fumarate reductase's ability to convert succinate to fumarate in E. ictaluri is not as efficient as compared to Salmonella and E. coli or E. ictaluri sdhC mutant is cleared from the fish before bacteria can activate fumarate reductase, or an anaerobic condition triggering use of fumarate reductase does not occur during fish infection. Our recent analysis of E. ictaluri proteome showed that many proteins involved in the tri-carboxylic acid (TCA) pathway including the fumarate reductase complex present and TCA pathway significantly represented in E. ictaluri (unpublished data). In E. coli sdhC mutants, SdhC activity is located in the cytoplasm, and it utilizes artificial electron acceptors; in contrast, wild-type E. coli has membrane-associated SdhC activity with ubiquinone as the electron acceptor. In E. coli, fumarate reductase is expressed under anaerobic conditions with glucose as a carbon source. Although SdhC has similar function, hydrophobicity, and protein size to the membrane-binding subunit from fumarate reductase (FrdC), SdhC and FrdC do not share significant sequence identity. In *Helicobacter pylori*, fumarate reductase was found to be essential for colonization of mouse gastric mucosa. In *E. coli* and *Salmonella*, succinate dehydrogenase is known to contribute to pathogenicity. The organic acids formate and succinate have a protective effect in stationary phase cells against killing effects of antimicrobial peptide BPI, which appears to disrupt the bacterial respiratory chain. Maintenance of protective levels of formate and succinate requires the activity of formate dehydrogenase and succinate dehydrogenase, respectively. *E. ictaluri* also encodes the formate dehydrogenase complex in its genome.

Mutants 2, 3, and 8 all had insertions in gcvP, which encodes a protein that is part of the glycine cleavage system. The glycine cleavage system is a loosely associated four subunit enzyme complex that catalyzes the reversible oxidation of glycine to form 5, 10-methylenetetrahydrofolate, which serves as a one carbon ("1C") donor. It is one of two sources of 1C units with serine hydroxymethyltransferase being the other (and is considered the more important source). Expression of the glycine cleavage enzyme system is induced by glycine, and gcv mutants are unable to use glycine as a 1C source and excrete glycine. The glycine cleavage system is also part of the formyltetrahydrofolate biosynthesis system. GcvP is a 104 kDa protein that catalyzes the decarboxylation of glycine. In *E. ictaluri*, gcvP is the third gene in a three gene operon; it is located downstream of gcvH and gcvT, which encode subunits of the glycine cleavage system. *E. ictaluri* also has a gene that encodes serine hydroxymethyltransferase. The glycine cleavage system has not been linked with virulence previously, and our disclosed composition and method are the first to employ it.

Mutant 1 had an insertion in rseB, which encodes one of two negative regulators of sigmaE. RseA is considered the major regulator of sigmaE. SigmaE is expressed in response to heat shock and other stresses on membrane and periplasmic proteins, including misfolding of outer membrane proteins, hyperosmotic stress, metal ion exposure, changes in LPS structure, and starvation signal ppGpp. SigmaE is required for heat-induced transcription of rpoH, which encodes heat shock factor sigma32 and other heat shock proteins. RseB is a periplasmic protein that interacts with RseA. RseB stimulates binding of RseA to sigmaE, thereby assisting RseA in tethering sigmaE to the cytoplasmic membrane. Degradation of RseA releases sigmaE and allows it to interact with the core enzyme of RNA polymerase to initiate transcription. Although mutations in rseA cause increased sigmaE activity, an rseB mutant shows wild-type sigmaE activity under inducing conditions and exhibits a small increase in sigmaE activity under non-inducing conditions. In *E. ictaluri*, rseB is the third gene in a polycistronic operon. It is downstream of rpoE, which encodes sigmaE, and rseA, and it is upstream of rseC, which encodes a positive regulator of sigmaE. SigmaE is required for *Salmonella* virulence and mediates *Salmonella* resistance to oxidative stress and antimicrobial peptides. SigmaE is also required for *Salmonella* to survive intracellularly. We disclose the first report of RseB being associated with virulence.

Mutant 6 has an insertion in rsxB, which encodes one of six proteins that form a SoxR reducing system in *E. coli*. SoxR is a regulatory protein that senses superoxide and nitric oxide and induces expression of an oxidative stress response. When SoxR is activated by oxidation of its [2Fe-2S] cluster, it induces expression of SoxS, which is a transcriptional regulator that induces expression of superoxide dismutase and other oxidative response proteins. The SoxR reducing system inactivates SoxR, thereby turning off the oxidative stress response. In *E. coli*, when any of the six rsx genes are mutated, SoxS is constitutively expressed, leading to induction of oxidative stress response. In *Salmonella*, SoxS is not essential for virulence, but SoxS was found to contribute to virulence in an *E. coli* mouse pyelonephritis model. In *E. ictaluri*, rsxB is the second in the six gene rsx operon.

Mutant 4 has an insertion in a gene encoding a hypothetical protein located on one of the two *E. ictaluri* constitutive plasmids, pEI1. The protein has >50% identity with *Salmonella* effector proteins with leucine rich repeats that are secreted through a type III secretion system. The 618 amino acid protein appears to be in a monocistronic operon.

EXAMPLE

Identifying Mutants that Fail to Attach to the Host Epithelium

The BLMS method can also be used to identify bacterial mutants that fail to attach to the host molecules, cells, or surfaces. Attachment and colonization of the host epithelium is an indispensable first step to any bacterial infection and can be achieved through a variety of diverse mechanisms. To investigate these attachment mechanisms in *Edwardsiella ictaluri*, we used random insertion of the pMar2xT7 transposon to generate a library of 1728 mutants. Each mutant expressed bioluminescence constitutively from the plasmid pAKlux1. This library was then screened in a high throughput fashion using an IVIS Living Image System (XENOGEN) in a series of nested in vivo challenges using a skin abrasion model we developed. Twenty mutants that displayed a decrease in their ability to colonize the channel catfish epithelium were identified. Results from this study will delineate mechanisms of *E. ictaluri* attachment to channel catfish skin and could lead to improved methods for prevention of enteric septicemia of catfish.

Combinations of Mutations. Combinations of mutations can be constructed using the pathways we have disclosed. Specifically, in-frame deletions in TCA cycle enzymes and glycine cleavage system protein can be constructed to create greater attenuation while retaining antigenicity. Mutation of the glycine cleavage system as a vaccine strategy is a new strategy that has never been previously reported. EiAKMut2 has a mutation in gcvP. The glycine cleavage system functions in providing 5,10-methylenetetrahydrofolate as a source for 1C moieties. Our plan is to construct a mutant containing deletions in gcvP (our current mutant) and in another enzyme that serves to provide 5,10-methylenetetrahydrofolate through an alternative pathway. Knocking out both pathways should cause improved attenuation.

Mutation of genes encoding TCA cycle enzymes, exemplified by EiAKMut05 and EiAKMut12, shows great potential as a strategy for an effective live attenuated *E. ictaluri* vaccine. Knockout of genes encoding TCA cycle enzymes was recently discovered as an effective strategy for vaccine development in *Salmonella* (which is closely related to *Edwardsiella*). We have found that knocking out a single TCA cycle gene does not always cause complete attenuation, but knocking out two genes can cause complete attenuation. Specifically, a *Salmonella* sdhCDA-frdABCD double mutant was fully avirulent and effective as a vaccine, while a *Salmonella* sdhCDA mutant was not fully attenuated. A combination mutant can be constructed that has deletions in sdhC (the gene mutated in EiAKMut05) and mdh (the gene mutated in EiAKMut12), as well as a second sdhC combination mutant that has a knockout in another enzyme that encodes a related TCA cycle enzyme.

Use of Other Bacterial Species as Live Attenuated Vaccines for Various Hosts

The method and compositions disclosed herein are not limited to *Edwardsiella ictaluri*, but can be used in other bacteria as well. Because the genes discovered in this research project are well conserved in bacteria, the mutation of these genes in other bacterial pathogens can be utilized for development of effective live attenuated vaccines to prevent other diseases. For example, *Salmonella enterica* is closely related to *Edwardsiella ictaluri* and is in the same bacterial family (*Enterobacteriaceae*). The pathogenesis of *salmonellosis* in mammals is also similar to the pathogenesis of enteric septicemia of catfish caused by *E. ictaluri*. The mutation of these genes in *Salmonella* will result in development of an effective live attenuated vaccine for prevention of *salmonellosis* in various animal hosts. Similarly, the genus *Yersinia* is also in the same family as *Edwardsiella* and *Salmonella*, and the disease pathogenesis of *Yersinia* is similar to enteric septicemia of catfish. Therefore, the mutation of these genes will be effective for development of live attenuated vaccines for *Yersinia pestis*, which causes bubonic plague in humans, *Y. enterocolitica* and *Y. pseudotuberculosis*, which cause gastrointestinal disease in humans and other mammals, and *Y. ruckeri*, which causes enteric redmouth disease in salmonid fish.

The mutation of these genes may be an effective strategy for development of live attenuated vaccines for pathogenic *Escherichia coli*, *Shigella flexneri*, and *Shigella dysenterieae*, which are also closely related to *E. ictaluri*. The mutation of these genes can also be used for development of live attenuated vaccines against *Francisella tularensis*, which causes tularemia in humans, because the disease pathogenesis is similar to enteric septicemia of catfish. Other bacterial pathogens that we anticipate mutation of these genes may be effective for development of live attenuated vaccines include *Pasteurella multocida*, *Mannheimia haemolytica*, *Histophilus somni*, *Haemophilus influenzae*, *Haemophilus ducreyi*, *Haemophilus parasuis*, *Actinobacillus pleuropneumoniae*, *Actinobacillus suis*, *Actinobacillus actinomycetemcomitans*, *Avibacterium paragallinarum*, *Moraxella catarrhalis*, *Moraxella bovis*, *Pseudomonas aeruginosa*, *Coxiella burnetii*, *Bordetella bronchiseptica*, *Bordetella pertussis*, *Bordetella parapertussis*, *Bordetella avium*, *Burkholderia mallei*, *Burkholderia pseudomallei*, *Neisseria meningitidis*, *Neisseria gonorrhoeae*, *Brucella abortus*, *Legionella pneumophila*, *Helicobacteri pylori*, and *Campylobacter jejuni*. Mutation of these genes may also be effective for development of live attenuated vaccines for gram-positive pathogens such as *Listeria monocytogenes*. In addition, BLMS may be an effective tool for identification of new gene targets for development of live attenuated vaccines.

Building on the BLMS method studies, we created bacterial mutant strains of the pathogenic bacterial strain of *Enterobacteriaceae*, *E. ictaluri*, harboring multiple gene disrupting (non-functional) mutations of the identified gene targets provided in the list of glycine cleavage system (gcvP), serine hydroxymethyltransferase, succinate dehydrogenase, malate dehydrogenase, 2-oxoglutarate dehydrogenase, negative regulator of sigma E activity (rseB), hypothetical protein pEI1_p1, electron transport complex protein RnfB, Fimbrial chaperon protein, Putative RNA one modulator protein pEI1_p4, UDP-glucose 6-dehydrogenase, fumarate reductase (frdA), and other genes encoding enzymes in the tri-carboxylic acid (TCA) cycle. Specifically, the gene coding for glycine cleavage system (gcvP) and three genes related to the TCA cycle, including succinate dehydrogenase (sdhC), malate dehydrogenase (mdh), and fumarate reductase (frdA), were targeted by in frame gene disrupting mutations to test live attenuated vaccines of *E. ictaluri* in farm-raised channel catfish. We constructed and tested double mutants of EiΔfrdAΔsdhC and EiΔgcvPΔsdhC, but these did not show the level of safety and efficacy as compared with the respective individual deletion mutants. By adding a third gene disrupting (non-functional) mutation, we synergistically increased safety and efficacy in fry and fingerling catfish to a level that was not additive of the individual mutants or the double mutants plus third mutants. This was unexpected, especially given the prior work in *S. enterica* showing complete attenuation with deletion mutations in succinate dehydrogenase and fumarate reductase. Even more surprising was that the triple mutant ESC-NDKL1 (ΔgcvPΔsdhCΔfrdA) strain was superior to the triple mutant ESC-NDKL2 (ΔgcvPΔsdhCΔmdh) strain because our previous work showed that individual gene disrupting mutants in the gcvP and mdh genes showed superior results compared to other single mutants. Also, the individual gene disrupting mutants in the sdhC gene showed no mortality in immunized fish. Thus, it would have been expected to have superior results for the ESC-NDKL2 (ΔgcvPΔsdhCΔmdh) strain, but the complex interplay of these pathways appears to have resulted in synergistic rather than mere additive effects on safety and efficacy in live attenuated vaccine trials.

The primary role of the TCA cycle is to provide NADH, which is used by bacterial cells for ATP synthesis via the electron transport chain for the complete catabolism of non-preferred carbon sources and the subsequent generation of reducing potential and biosynthetic intermediates. Also, several enzymes of TCA cycle require iron, for example, aconitase, succinate dehydrogenase complex, and fumarase. Thus, during growth under conditions of low iron availability, the TCA cycle activity was dramatically reduced (Somerville et al., 1999; Varghese et al., 2003). In a previous study, culturing *Staphylococcus epidermidis* with an increasing TCA cycle stimulator fluorocitrate dramatically decreased polysaccharide intercellular adhesion (PIA) synthesis and biofilm production without impairing glucose catabolism, the growth rate, or the growth yields (Zhu et al., 2009), which lead to speculation that *S. epidermidis* perceives environmental changes through alterations in TCA cycle activity, leading to changes in the intracellular levels of biosynthetic intermediates, ATP, or the redox status of the cell (Vuong et al., 2005). These changes in the metabolic status of the bacteria result in attenuation. Recent studies using serovar *Typhimurium* (*Salmonella enterica*) described that mutant stains with a deletion of genes encoding TCA cycle enzymes Δmdh, ΔsucCD, and ΔsdhCDAB replicated to higher levels than the wild-type in resting and activated macrophages, which suggests an enhanced ability to survive under antimicrobial conditions (Bowden et al., 2010). *S. enterica* ΔfrdABCDΔsdhCDA double mutants with complete TCA cycles may exhibit to be effective live vaccine strains for animal and human like ΔfrdABCDΔsdhCDA double mutants of other intracellular bacterial pathogens (Mercado-Lubo et al., 2008). In *Helicobacter pylori*, fumarate reductase was found to be essential for colonization of mouse gastric mucosa (Ge et al., 2000). These data suggest that the conversion of succinate to fumarate plays a key role in bacterial virulence.

Previously, we conducted immersion trials in catfish fingerlings by using EiΔsdhC, EiΔfrdA, EiΔfrdAΔsdhC, and EiΔgcvPΔsdhC mutants as part of or continuing research of the BLMS method findings, which provided significant protection against wild-type *E. ictaluri* (Dahal et al., 2014; Dahal et al., 2013). These bacterial mutants retained the ability to penetrate catfish mucosa and persist and colonize posterior kidney similar to wild-type *E. ictaluri*, suggesting that attenuation is not due to mutants' inability to invade the host. In our previous report, similar results were observed with transposon insertion mutants (Karsi et al., 2009). However, our previous study showed that catfish fry (<15 days post hatch) were more sensitive to *E. ictaluri* than fingerlings, due to immaturity of the acquired immune organs as lymphoid populations in the anterior renal haematopoietic tissue, and the first appearance of splenic red and white pulp compartmentalisation in fry (Patrie-Hanson and Jerald Ainsworth, 1999). Of the combination mutants, only EiΔgcvPΔsdhC showed safety in catfish fry over 30% mortality and provided protection against *E. ictaluri* infection post-immunization. This was unexpected; therefore, the current work aimed to improve the safety and efficacy of EiΔgcvPΔsdhC by constructing a combination of triple mutants associated with TCA cycle and C1 metabolism protein derivated from EiΔgcvPΔsdhC against wild-type *E. ictaluri* infection in catfish fry and fingerling.

The vaccine trials conducted under laboratory conditions indicated that immersion immunization of channel catfish fry and fingerling with ESC-NDKL1 (ΔgcvPΔsdhCΔfrdA) provided significant safety and protection. Fumarate reductase (frd) and succinate dehydrogenase (sdh) are physiologically reversible isoenzymes in the TCA cycle that are induced under anaerobic and aerobic respiratory chain, which can replace each other with functionally related membrane-bound enzyme complexes (Guest, 1981; Maklashina et al., 1998; supra). Both enzyme complexes contain a catalytic domain composed of a subunit with a covalently bound flavin cofactor, the dicarboxylate binding site, and an iron-sulfur subunit, which contains three distinct iron-sulfur clusters, and the catalytic domain is bound to the cytoplasmic membrane by two hydrophobic membrane anchor subunits that also form the site for interaction with quinones (Cecchini et al., 2002). Glycine cleavage system (gcv) serves as a one carbon donor (C1 unit); serine hydroxymethyltransferase is another one carbon donor source (supra). Expression of the glycine cleave enzyme system is induced by high concentrations of glycine, and a gcv mutant was unable to use glycine as a C1 source and excrete glycine (Meedel and Pizer, 1974; Plamann et al., 1983; Stauffer et al., 1994), and we have shown that *E. ictaluri* gcvP is required for virulence (Karsi et al., 2009).

The laboratory challenge was followed by a field trial mimicking commercial catfish production to evaluate the efficacy of the ESC-NDKL1 (ΔgcvPΔsdhCΔfrdA) in earthen pond conditions, the best vaccination regime (immersion, oral, and immersion-oral combination), and also, compare the efficacy of the ESC-NDKL1 to the commercially available vaccine, AQUAVAC-ESC. Under field conditions, the fry were vaccinated with an ESC-NDKL1 by immersion (19 days post-hatch) in the early summer, and the oral booster was included in late summer (80 days post-hatch). This vaccination schedule time was chosen to provide protection during the high incidence ESC season that occurs in the late spring and early fall when water temperatures are in the 18-28° C. range, the optimal temperature range for ESC development (Plumb, 1988; Thune et al., 1994).

During the 95 days of the pond study, there was no difference between the five earthen ponds considering the water quality parameters. Overall means of DO and temperature are within what is expected for catfish fingerling production under commercial conditions (Tucker, 1990). The results from field study depend on the survival of fingerlings in each pond at the end of the study. The probability of survival depends on the initial stocking number (300 fish/pen) and remaining number at the harvest. The daily dead fish cannot be gathered in this study. Other production parameters such as the mean of total weight, individual fish weight, and individual fish length were also taken into consideration as an indication of vaccination benefits.

The field study indicated the ESC-NDKL1 (ΔgcvPΔsdhCΔfrdA) vaccination improved survival in the pond by approximately 5.96, 8.76, and 26.67 times the oral, immersion, and immersion-oral combination, respectively. The three ESC-NDKL1 vaccinated ponds were significantly protected compared to sham-vaccinated, and the AQUA-VAC-ESC vaccinated ponds. Further supporting the survival results, the mean total weight for fish ponds vaccinated with the ESC-NDKL1 strain (immersion, oral, and immersion-oral) were higher than the sham-vaccinated, and the AQUA-VAC-ESC vaccinated fish ponds, which indicated that vaccinated populations grew better than the non-vaccinated fish and commercially available vaccine.

Comparing the survival and total weight of the three ESC-NDKL1 (ΔgcvPΔsdhCΔfrdA) vaccination strategies showed that better survival of immersion-oral combination (95.22% survival) vaccination over oral vaccination (81.67% survival) and immersion vaccination (86.74% survival). Although statistical differences were not observed, especially when comparing small numbers of fish, economic benefits may exist. This observation is consistent with the study using an *E. ictaluri* killed bacteria vaccine indicated that immersion vaccination followed by an oral booster administered through the feed resulted in lower mortality and higher agglutinating antibody titers compared with an immersion-only or non-vaccinated fish (Plumb, 1993).

The catfish pond vaccinated by ESC-NDKL1 (ΔgcvPΔsdhCΔfrdA) through immersion showed better survival than an oral vaccinated pond. This could be due to the vaccination by immersion ensures that all fish are exposed to the vaccine, but feeding vaccination does not ensure that all fish receive the vaccine strain. Indeed, it is important to note that the immersion vaccination with ESC-NDKL1 strain provided significant protection against ESC even after four months from exposure under field trials, this is a great advantage over the currently available vaccine.

In this study, the mean individual fish weight of thirty fish was observed to be higher in the three ESC-NDKL1 (ΔgcvPΔsdhCΔfrdA) vaccinated ponds (immersion, oral, immersion-oral) and AQUAVAC-ESC than the sham-vaccinated group. Similarly, the individual fish lengths obtained from the ESC-NDKL1 vaccinated ponds were higher than a sham-vaccinated pond, although statistically analysis showed no significant differences.

A critical factor not evaluated in this study is the claim that the delay in fry stocking and use of a primary nursery phase can reduce early fry mortality and reduce unaccounted fish losses (Morrison et al., 1995). A typical production cycle for channel catfish industry involves the stocking of 7 to 10 days old fry directly into earthen ponds and growing them for 5 to 10 months. However, this method has resulted in high levels of mortality during the first 30 days (Carpenter, 2001). In the present study, we stocked the fry in the earthen pond at 50 days post-hatch. Using oral-immersion as an example, 4.39% of fry that died from the stocking until the time of harvesting from the ponds. This shows that the use of the nursery phase results in less fry mortality during the first 30 days than stocking fry directly into ponds (Morrison et al., 1995).

AQUAVAC-ESC was included in this study for comparison. The field study is, however, somewhat difficult to directly compare with other similar studies because there are different aspects that vary from one study to another such as stocking density, the length of growing period, quality of feed utilized, management techniques, and water parameters. Past studies have shown that AQUAVAC-ESC (RE-33) provides protection in fish against virulent E. ictaluri isolates when vaccinated 7 to 72 days post-hatch based on laboratory findings and limited field studies (Shoemaker et al., 1999; Wise et al., 2000). For example, a laboratory study reported that 12-day old fry vaccinated by AQUAVAC-ESC via immersion with a dosage between $5 \times 10^5$ and $1 \times 10^6$ CFU/mL resulted in lower mortality (33.3%) than that of a non-vaccinated group (78.7%) (Shoemaker et al., 1999). In another study, 72-day old fry vaccinated by AQUAVAC-ESC at a dose of $1 \times 10^6$ reported a lower percent mortality (58.5%) for the vaccinated group as compared to the non-vaccinated group (77.5%) in the laboratory. In a second part of this same study under field conditions, 21-day old, vaccinated fry resulted in no protection, as shown by similar percent mortalities after exposure to an E. ictaluri epizootic occurring in a commercial catfish pond (Wise et al., 2000).

In conclusion, our laboratory and field studies showed that ESC-NDKL1 (ΔgcvPΔsdhCΔfrdA) strain with mutations in combined TCA cycle enzymes and C1 metabolism protein was significantly attenuated and provided vaccine efficacy against ESC. The field study also showed that immersion vaccination followed by oral booster increased survival of catfish when they were exposed to the pathogenic bacterium. ESC-NDKL1 is a strong candidate for use as a live attenuated vaccine for catfish fry and fingerling in commercial hatcheries and fish farms.

EXAMPLE

Live Attenuated Triple Mutant Vaccine for Use in Catfish

The following description more particularly discloses the steps used in practicing the claimed triple mutant E. ictaluri live attenuated vaccines.

Materials and Methods

Bacterial Strains, Plasmids, and Growth Conditions. Bacterial strains and plasmids used in this study are listed in TABLE 3. E. ictaluri was grown at 30° C. using brain heart infusion (BHI) broth and agar (Difco, Sparks, Md.). Escherichia coli were grown at 37° C. using Luria-Bertani (LB) broth and agar (Difco). E. coli CC118 λpir and SM10 λpir/S17-1 λpir were used for cloning mutated fragments into the pMEG-375 plasmid and conjugal transfer of pMEG-375 suicide plasmid into E. ictaluri. Ampicillin was used at 100 µg/ml to maintain pMEG-375, and colistin was used at 12.5 µg/ml for counter selection against E. coli SM10 λpir following conjugation.

TABLE 3

Bacterial strains and plasmids.

| Strain | Relevant Characteristics | References |
|---|---|---|
| *Edwardsiella ictaluri* | | |
| 93-146 | Wild-type; pEI1$^+$; pEI2$^+$; Col$^r$ | (Lawrence et al., 1997) |
| EiΔgcvPΔsdhC | 93-146 derivative; pEI1$^+$; pEI2$^+$; Col$^r$; ΔgcvP ΔsdhC | (Dahal et al., 2014) |
| EiΔgcvPΔsdhCΔfrdA | 93-146 derivative; pEI1$^+$; pEI2$^+$; Col$^r$; ΔfrdAΔgcvP ΔsdhC | This study |
| EiΔgcvPΔsdhCΔmdh | 93-146 derivative; pEI1$^+$; pEI2$^+$; Col$^r$; ΔgcvP ΔsdhCΔmdh | This study |
| *Escherichia coli* | | |
| CC118 λpir | Δ(ara-leu); araD; ΔlacX74; galE; galK; phoA20; thi-1; rpsE; rpoB; argE(Am); recA1; λpirR6K | (Herrero et al., 1990) |
| SM10 λpir | thi; thr; leu; tonA; lacY; supE; recA; ::RP4-2-Tc::Mu; Km$^r$; λpirR6K | (Miller and Mekalanos, 1998) |
| S17-1 λpir | RP4-2 (Km::Tn7, Tc::Mu-1), ΔuidA3::pir$^+$, recA1, endA1, thi-1, hsdR17, creC510 | (Metcalf et al., 1994) |
| Plasmids | | |
| pMEG-375 | 8,142 bp, Amp$^r$, Cm$^r$, lacZ, R6K ori, mob incP, sacR sacB | (Dozois et al., 2003) |
| pEiΔfrdA | 10,242 bp, ΔfrdA, pMEG-375 | (Dahal et al., 2013) |
| pEiΔmdh | 8,981 bp, Δmdh, pMEG-375 | (Dahal et al., 2013) |

Construction of in-frame deletion mutants. Overlap extension PCR (Horton et al., 1990) was used to generate in-frame deletions of E. ictaluri genes. EiΔgcvPΔsdhC mutant and plasmids with ΔfrdA and Δmdh fragments (pEiΔfrdA and pEiΔmdh) were reported previously (Dahal et al., 2013; incorporated herein by reference for all that it teaches that is not contradictory to the present disclosure). pEiΔfrdA and pEiΔmdh were mobilized into double mutant EiΔgcvPΔsdhC by conjugation (for methods, see Karsi and Lawrence, 2007; incorporated herein by reference for all that it teaches that is not contradictory to the present disclosure). The recipient bacteria were spread on BHI agar containing colistin and ampicillin for selecting *E. ictaluri* with integrated vector, and positive colonies were followed by streaking on BHI agar with 5% sucrose and 0.35% mannitol for allelic exchange and loss of pMEG-375 with the sacB gene. Deleted regions were amplified from the resulting ampicillin sensitive colonies and confirmed by sequencing. The two triple mutants evaluated in this study were named as ESC-NDKL1 (EiΔgcvPΔsdhCΔfrdA) and ESC-NDKL2 (EiΔgcvPΔsdhCΔmdh).

Safety and efficacy of the ESC-NDKL1 (EiΔgcvPΔsdhCΔfrdA) and ESC-NDKL2 (EiΔgcvPΔsdhCΔmdh) in catfish in laboratory trials. Vaccine safety in specific pathogen free (SPF) catfish fry (3.17±0.05 cm, 335.92±20.02 mg) and fingerlings (7.75±0.08 cm, 4,500±14.07 mg) was determined for the two triple mutants and commercial live attenuated vaccine (Klesius and Shoemaker, 1999). One treatment group was used as a sham control. 14-day old catfish fry were stocked into 20 tanks at a rate of 40 fish/tank, and three-month-old catfish fingerlings were stocked into 20 tanks at a rate of 25 fish/tank. Fry experiment included four replicates and fingerling experiment included three replicates per group. Experiments were conducted in 40-L tanks supplied with flow-through water and fed two times per day. Water temperature was adjusted to 25° C. throughout the experiments. Vaccination doses were $6.0 \times 10^6$ CFU/ml water and $4.5 \times 10^7$ CFU/ml water for catfish fry and fingering, respectively. Mortalities were recorded daily for 21 days, and swab samples from the dead fish were plated on BHI agar for confirmation of the causative pathogen. At 21 days post-vaccination, vaccinated and sham control groups were immersion exposed to Wt *E. ictaluri* 93-146 containing $3.8 \times 10^7$ CFU/ml water, and fish mortalities were monitored daily for 21 days. Relative percent survival (RPS) was calculated according to the following formula: RPS=[1−(% mortality of vaccinated fish/% mortality of non-vaccinated fish)]×100.

Determine efficacy of the ESC-NDKL1 (EiΔgcvPΔsdhCΔfrdA) in catfish fry under commercial pond culture conditions. Pond preparation: five identical earthen ponds (0.12 acre each, with an average depth of 1.5 m) located at the South Farm Aquaculture Research Facility at Mississippi State University were used to grow catfish fry into fingerlings. The designated ponds (A13, B3, B11, B12, and B13) were drained and dried four weeks before stocking. The ponds were supplied with groundwater. Three weeks before stocking the ponds were fertilized with Perfect Pond Plus Fertilizer (Alabama, USA) and dissolved oxygen was measured daily before stocking. Supplemental aeration was provided to each pond by Air-O-Lator 24 h and seven days week. We placed four square pens (4×4×4 feet) in each pond representing four replicates for each treatment for statistical comparisons. The four pens in each pond were located in a square pattern around the Air-O-Lator to enhance the aeration in the pens and remove dissolved oxygen as a factor in mortality counts. The pens were covered with a lid to prevent birds and other animals from preying on the fish.

Water quality management: throughout the experiment, the ponds were managed according to industry practices. Dissolved oxygen (DO) and temperature were monitored twice daily in the morning and afternoon using a with a portable dissolved oxygen meter (YSI model 550A, YSI Inc., San Diego, Calif.) on the pond bank. Water was added to the ponds periodically to replace that which was lost through evaporation and seepage.

Stocking of the fry and vaccination schedule: on Jun. 25, 2015, approximately 6,000 17 day-old specific pathogen free (SPF) catfish fry were stocked into five tanks (1200/tank) supplied with flow-through dechlorinated water. Water temperature was maintained at 25-26° C. throughout indoor conditions. The five tanks corresponded to five treatment groups (immersion, oral, immersion-oral combination, commercial vaccine, and sham-vaccinated). On Jun. 27, 2015, catfish fry (19 days post-hatch) in three treatment groups (immersion, immersion-oral, and commercial) were immersion vaccinated indoors ($3.93 \times 10^7$ CFU/ml of water for 1 h). Fry in the sham-vaccinated group were exposed to an equivalent volume of brain heart infusion (BHI) broth indoors. The tanks were observed daily for mortalities. Fry in all treatments were moved to the ponds on Jul. 27, 2015. The fry were transferred in aerated containers and stocked into ponds at a rate of 1200 fry/pond (300 fry/pen). The pens were covered with a lid to prevent birds and other animals from preying on the fish.

Feeding: fish were fed twice a day by hand, once in the morning and afternoon, with a commercial catfish feed. Changing to a larger feed pellet was determined according to the behavior and size development of the fry in each pond. Fish were observed after feeding, and the activity of feeding was documented.

Vaccine preparation and oral vaccination: to prepare oral vaccination, an overnight culture of ESC-NDKL1 (ΔgcvPΔsdhCΔfrdA) containing $3.52 \times 10^9$ CFU/ml was mixed with commercial feed pellets at a rate of 20% (weight to volume). The vaccine-feed was mixed by a hand mixer until all liquid was absorbed. The average amount of feed consumed one week before vaccination was used to estimate the amount of feed to use on vaccination days. On Aug. 21, 2015, oral vaccination was conducted for two groups (oral, and immersion-oral) by feeding vaccine-feed daily for five days (average feed 500 g/pond for five days), followed by five days feeding with no vaccine, and followed by five days feeding with vaccine. The other ponds were fed similarly but without adding the vaccine to feed.

ESC Challenge: on Sep. 26, 2015 (three months after immersion vaccination, and 35 days following the initial oral-vaccination), when water temperatures were conducive for *E. ictaluri* infection (22-24° C.), fish were challenged with wild-type *E. ictaluri* strain 93-146 in the feed. Overnight culture of wild-type *E. ictaluri* containing $2.71 \times 10^9$ CFU/ml was mixed with commercial feed at a rate of 20% (weight to volume), and each pond was fed for five consecutive days (average feed 600 g/pond for five days) followed by a five-day break, then another five days of exposure. Following vaccination, fish were fed regular feed without adding the vaccine to feed for 21 days.

Harvesting the ponds and measuring procedures: the study was terminated on Nov. 1, 2015 (35 days after wild-type infection) when the water temperature was less than 18° C. Fingerling fish were collected after three months of growing in net pens in earthen ponds. At the end of the trial, fish were harvested and euthanized in water containing 300 mg/L MS-222, and fish numbers and body measurements were collected. Thirty individual fish, representing 10% of the initial stocking population, from each pen, were selected randomly to determine the average individual weight and length. Body weight was determined to the nearest 0.1 g, and length was measured to the nearest 1 mm. The mortality rate for each pen was determined based on initial stocking numbers and numbers of remaining fish in each pen at the end of the study.

Statistical analysis. In the laboratory experiment, the effect of treatment on time to death was analyzed using survival analysis. Separate models were developed for fry safety, fry efficacy, fingerling safety, and fingerling efficacy. The Kaplan-Meier estimator was used to estimate the survivor functions using PROC LIFETEST, SAS for Windows 9.4 (SAS Institute, Inc., Cary, N.C., USA). The data for all outcomes was right censored at 21 days post-vaccination or post-challenge. The log-rank test and Wilcoxon test statistics were used to assess the effect of treatment. When treatment was found to have a significant effect, Dunnett's adjustment for multiple comparisons was used to compare each of the treatments to wild-type. The survivor functions were graphically displayed as Kaplan-Meier plots using PROC SGPLOT. An alpha level of 0.05 was used to determine statistical significance for all analyses.

In the field study, the effect of the different treatments on the survival of fish was assessed with mixed model logistic regression using PROC GLIMMIX in SAS for Windows 9.4 (SAS Institute, Inc., Cary, N.C., USA). The number of live fish in a replication at the end of the trial was the outcome assessed using an events/trials syntax. Treatment was the fixed effect evaluated in the model. Replication within a treatment group was included as a random effect in the model. The BHI (sham) and AQUAVAC-ESC treatment groups were the referents for comparisons of the effect of the other treatments using an LSMestimate statement. The results of the analysis were presented as odds ratios for survival and probability of survival.

The effect of the different treatments on the total weight of fish within a replication at the end of the trial was assessed by analysis of variance using PROC GLIMMIX in SAS for Windows 9.4. The results of the analysis were presented as least squares means and their standard errors. The BHI (sham) and AQUAVAC-ESC treatment groups were the referents for comparisons of the effect of the other treatments using an LSMestimate statement, adjusting the p-values for multiple comparisons with the simulate option.

The effects of the different treatments on the weight and length of 30 fish within a replication at the end of the trial were assessed in separate mixed model analyzes using PROC GLIMMIX in SAS for Windows 9.4. Treatment was the fixed effect assessed in each model while replication within a treatment group was included as a random effect. The results of the analysis were presented as least squares means and their standard errors. The BHI (sham) and AQUAVAC-ESC treatment groups were the referents for comparisons of the effect of the other treatments using an LSMestimate statement, adjusting the p-values for multiple comparisons with the simulate option.

The distribution of the conditional residuals was evaluated for each model to determine the appropriateness of the statistical model for the data. A significance level of 0.05 was used for all analyses.

Figure 4:
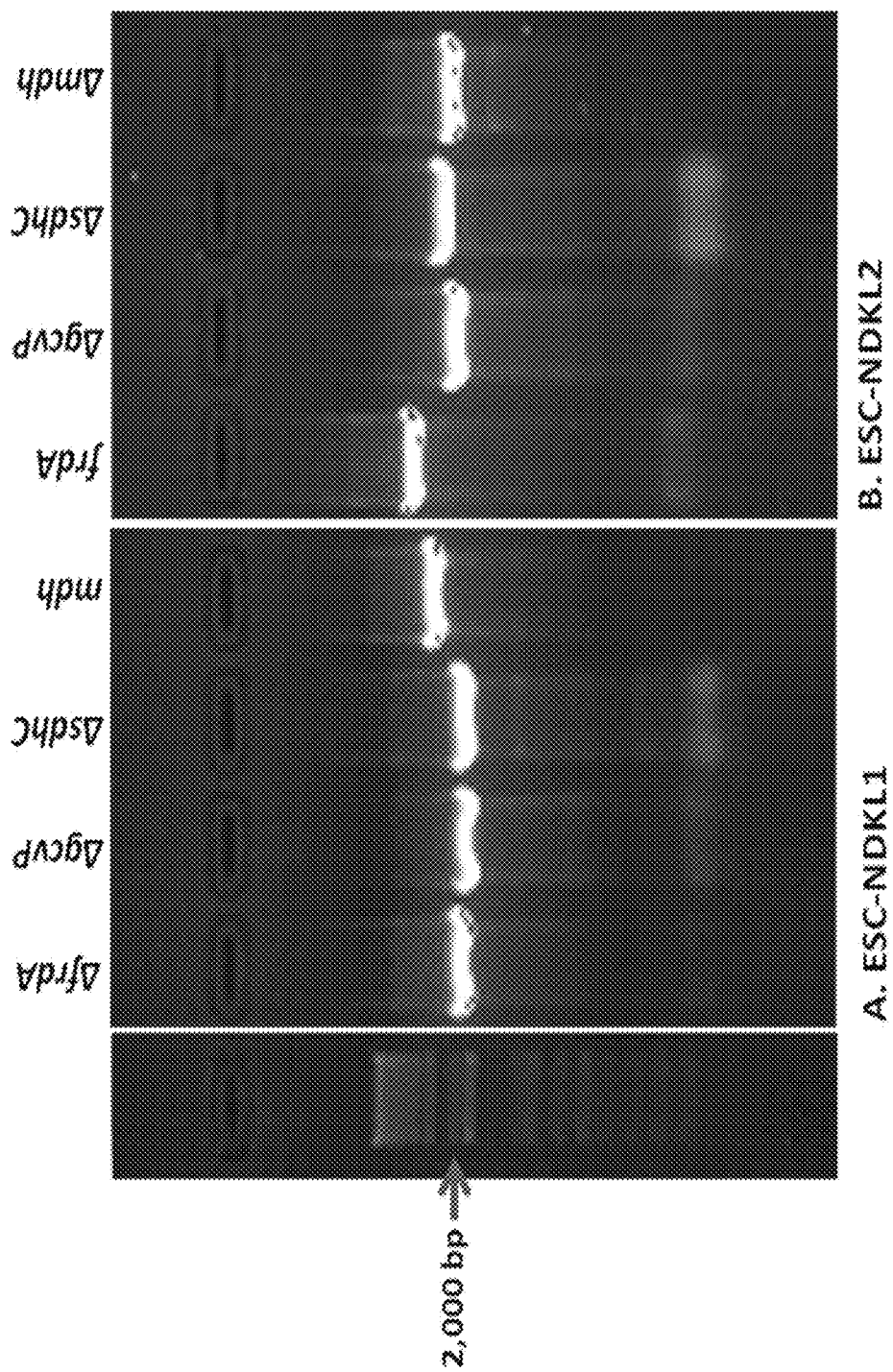

Construction of the *E. ictaluri* ESC-NDKL1 and ESC-NDKL2 strains. Two triple mutants ESC-NDKL1 (Ei$\Delta$gcvP$\Delta$sdhC$\Delta$frdA) and ESC-NDKL2 (Ei$\Delta$gcvP$\Delta$sdhC$\Delta$mdh) were constructed successfully (see FIG. 4). A large majority of the frdA (95.44%) and mdh genes (89.74%) were confirmed to be deleted in-frame (see TABLE 4).

TABLE 4

Properties of selected *E. ictaluri* TCA cycle and C1 metabolism genes and percentage of gene deleted.

| Gene | Locus | Product | ORF (bp/aa) | Remaining (bp/aa)* | % Deletion |
|---|---|---|---|---|---|
| frdA | NT01EI_0392 | Fumarate reductase, flavoprotein subunit, putative | 1800/899 | 126/41 | 95.44 |
| gcvP | NT01EI_3351 | Glycine dehydrogenase, putative | 2884/960 | 114/37 | 96.15 |
| sdhC | NT01EI_2872 | Succinate dehydrogenase, cytochrome b556 subunit, putative | 390/129 | 57/18 | 86.05 |
| mdh | NT01EI_0446 | Malate dehydrogenase, NAD-dependent, putative | 939/312 | 99/32 | 89.74 |

Figure 5A:
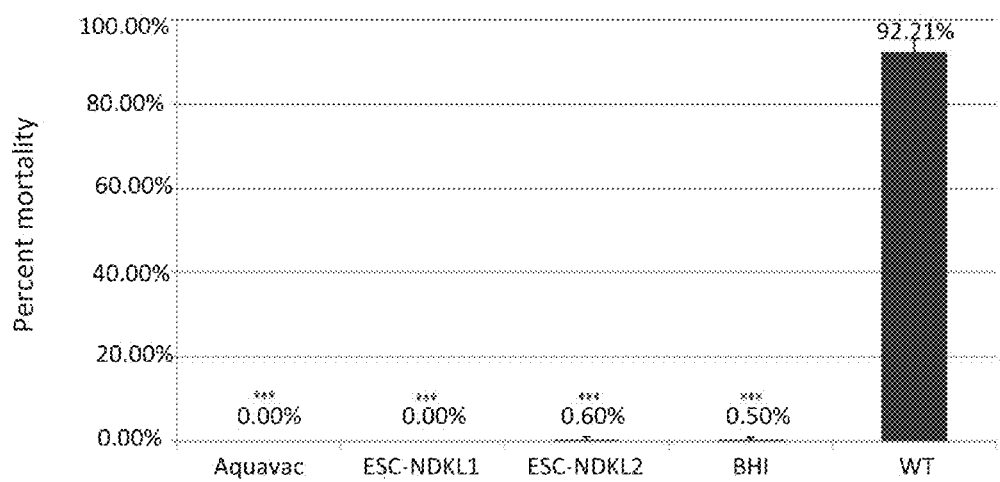
Figure 5B:
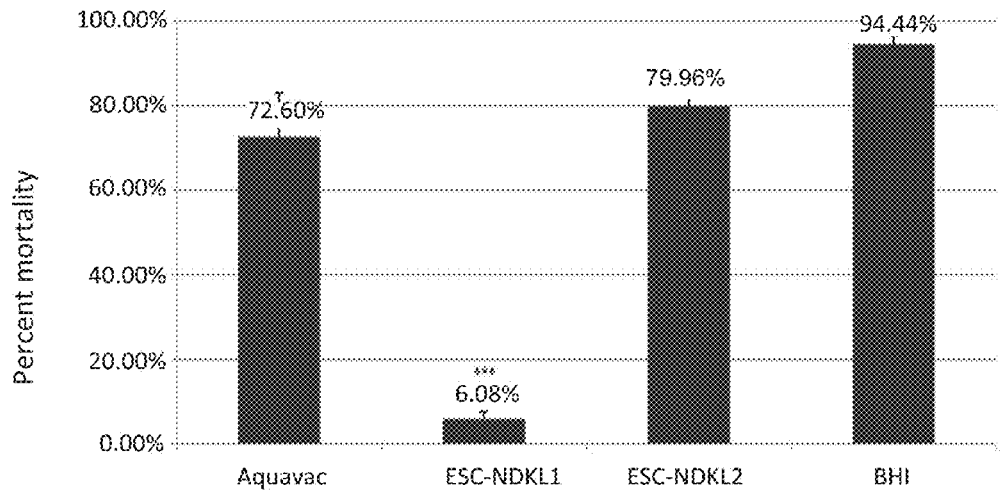

*Number of bp/aa remaining from genes following deletion by overlap extension PCR Safety and efficacy of ESC-NDKL1 and ESC-NDKL2 in catfish. The ESC-NDKL1 ($\Delta$gcvP$\Delta$sdhC$\Delta$frdA) and AQUAVAC-ESC showed no mortality in catfish fry vaccination while very low mortalities in ESC-NDKL2 ($\Delta$gcvP$\Delta$sdhC$\Delta$mdh) (0.6%) and sham control (0.5%) were observed. These results indicated that ESC-NDKL1 and ESC-NDKL2 were safe in catfish fry (see FIG. 5A). To determine vaccine efficacy of ESC-NDKL1 and ESC-NDKL2, fry were challenged with wild-type *E. ictaluri* by immersion exposure three weeks after vaccination. Fry were protected significantly (p<0.005) by ESC-NDKL1 vaccination with 6.08% mortality while the mortality in the sham vaccinated group was 94.44%. The ESC-NDKL2 and AQUAVAC-ESC mutants showed lower but similar protection rates at 72.60% and 79.96%, respectively (FIG. 5B).

Figure 6A:
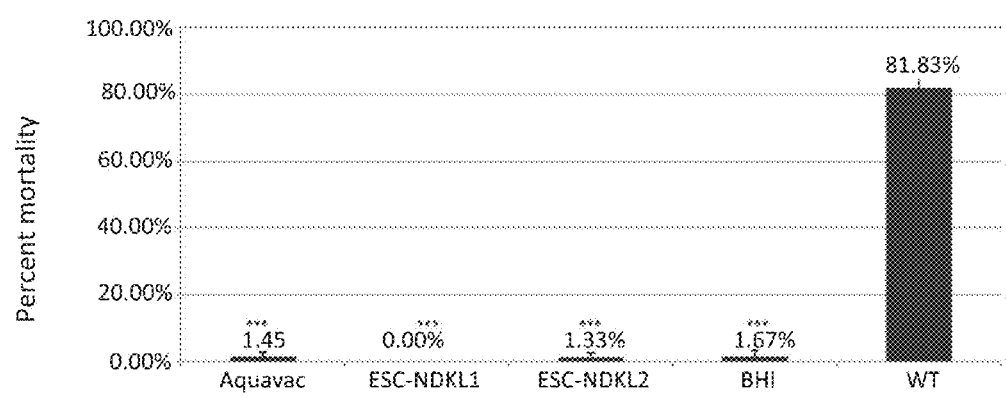
Figure 6B:
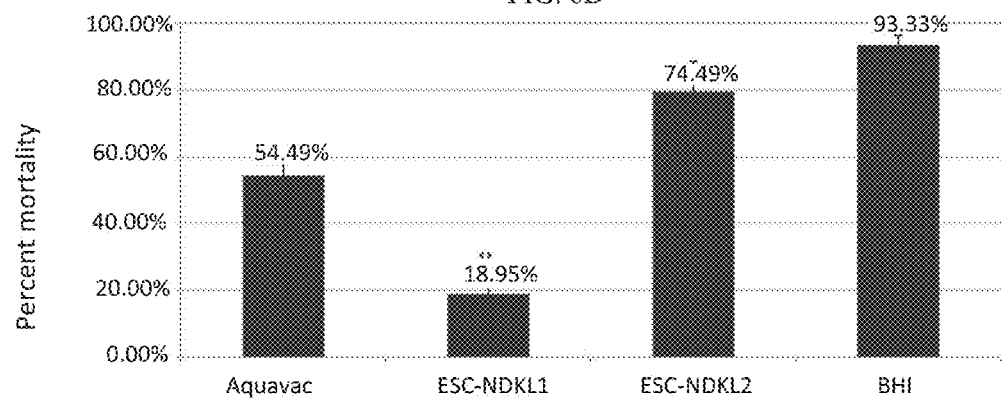

Fingerlings also showed similar results: ESC-NDKL1 ($\Delta$gcvP$\Delta$sdhC$\Delta$frdA) vaccination showed no mortality, while ESC-NDKL2 ($\Delta$gcvP$\Delta$sdhC$\Delta$mdh), AQUAVAC-ESC, and sham vaccination showed small percent mortalities (1.45%, 1.33%, and 1.67%, respectively). The mortality rate in wild-type challenged fingerlings was over 81% (see FIG. 6A). The vaccine efficacy of the mutants was determined by challenging vaccinated fingerling with wild-type *E. ictaluri* by immersion three weeks after vaccination. ESC-NDKL1 mutant protected fingerlings significantly (p<0.01) compared to ESC-NDKL2 and AQUAVAC-ESC. The ESC-NDKL1 vaccinated group showed 18.95% mortality while the ESC-NDKL2 and AQUAVAC-ESC showed 79.47% and 54.49% mortalities, respectively (FIG. 6B).

Figure 7A:
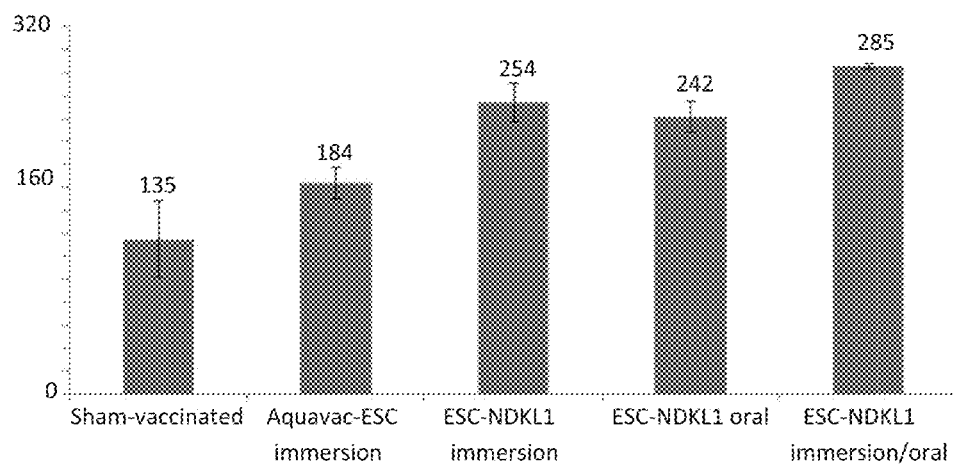
Figure 7B:
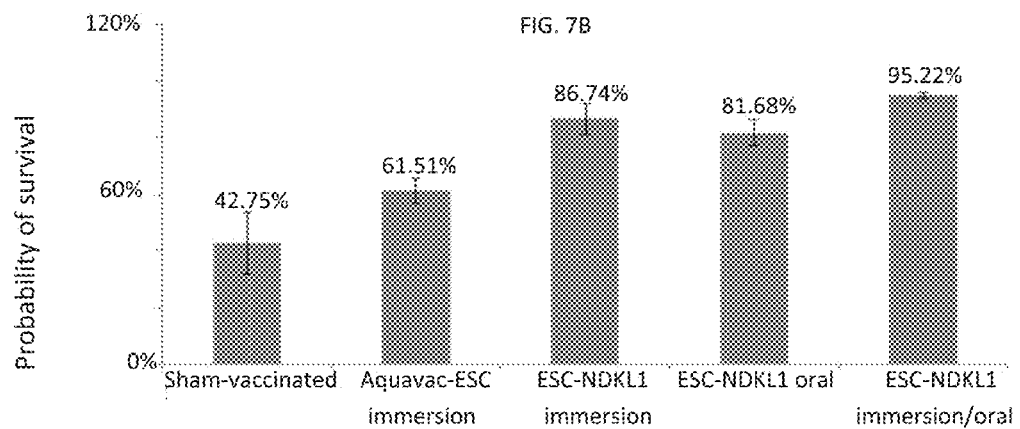

The efficacy ESC-NDKL1 ($\Delta$gcvP$\Delta$sdhC$\Delta$frdA) vaccine in catfish in earthen ponds. When the study was terminated and ponds harvested, an average of 254 fish/pen (86.74% probability of survival) remained in the ESC-NDKL1 immersion vaccinated pond, 242 fish/pen (81.67% probability of survival) remained in the ESC-NDKL1 oral vaccinated pond, and 285 fish/pen (95.22% probability of survival) remained in the ESC-NDKL1 immersion-oral combination vaccinated pond. This was significantly higher from both the average of 135 fish/pen (42.75% probability of survival) remained in the sham-vaccinated pond (p<0.05) and 184 fish/pen (61.51% probability of survival) remained in the AQUAVAC-ESC vaccinated pond (p<0.05). Conversely, there was no significant difference in the probability of survival between the AQUAVAC-ESC vaccinated pond and sham-vaccinated pond (p<0.1092) (see FIGS. 7A & 7B).

Figure 8:
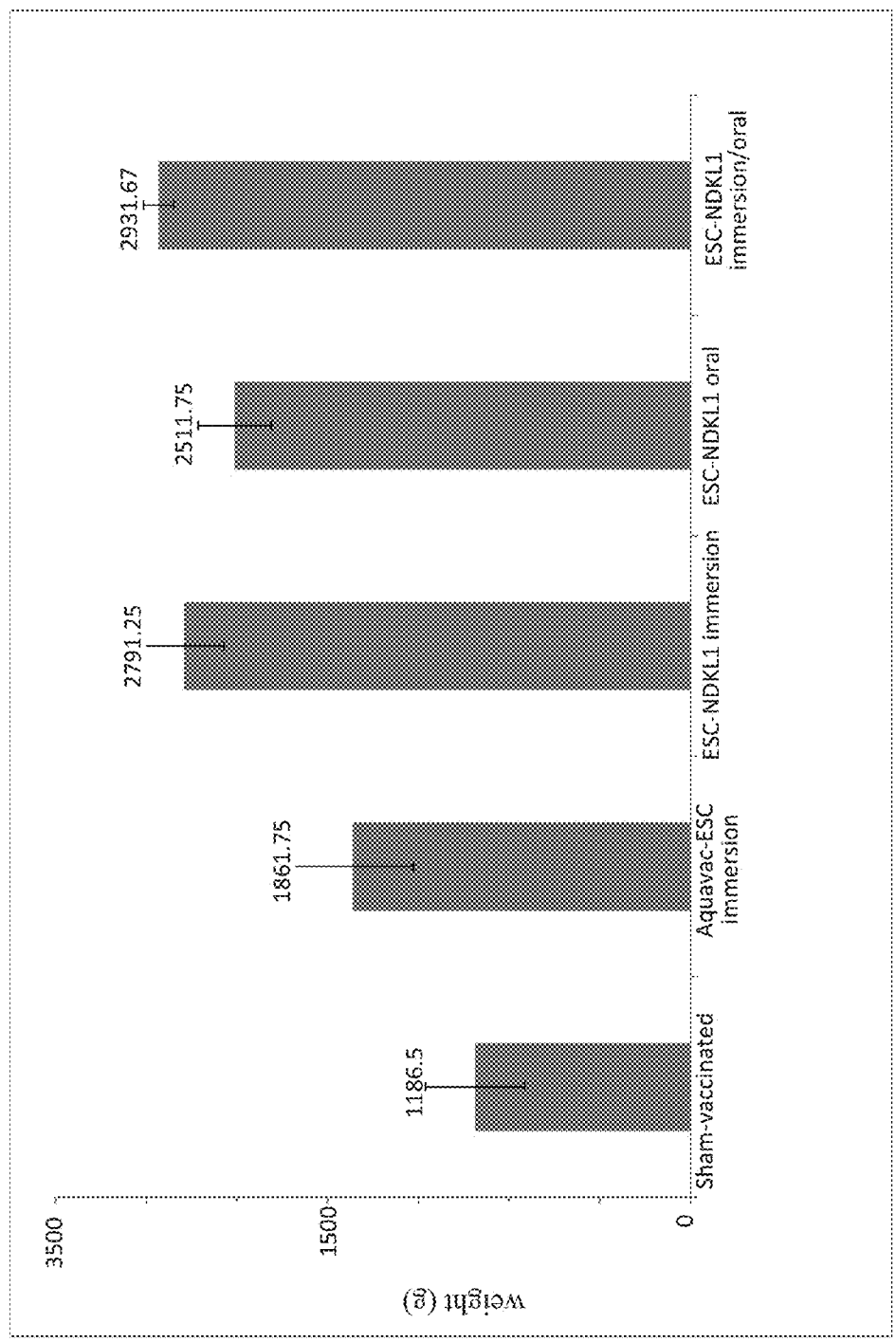
FIG. 8 is a bar graph showing the mean total weight of fish per pen at harvest. This data represents the mean of four replicate pens in each pond.

The mean total weight for each pen for fish vaccinated with the ESC-NDKL1 (ΔgcvPΔsdhCΔfrdA) by immersion (2791.25 g), oral (2511.75 g), and immersion-oral combination (2931.6 g) were significantly higher (p<0.0002, 0.0016, and 0.0002, respectively) than sham-vaccinated pond (1186.5 g). While no significant difference was found in the total weight observed between three ESC-NDKL1 vaccinated ponds (oral, immersion, and immersion-oral combination) compared with each other, there was a significant difference between the ESC-NDKL1 vaccinated ponds (oral, immersion, and immersion-oral combination) ponds and the AQUAVAC-ESC vaccinated pond (1861.75 g) (p<0.2559, 0.0414, and 0.0267, respectively) (see FIG. 8).

Figure 9:
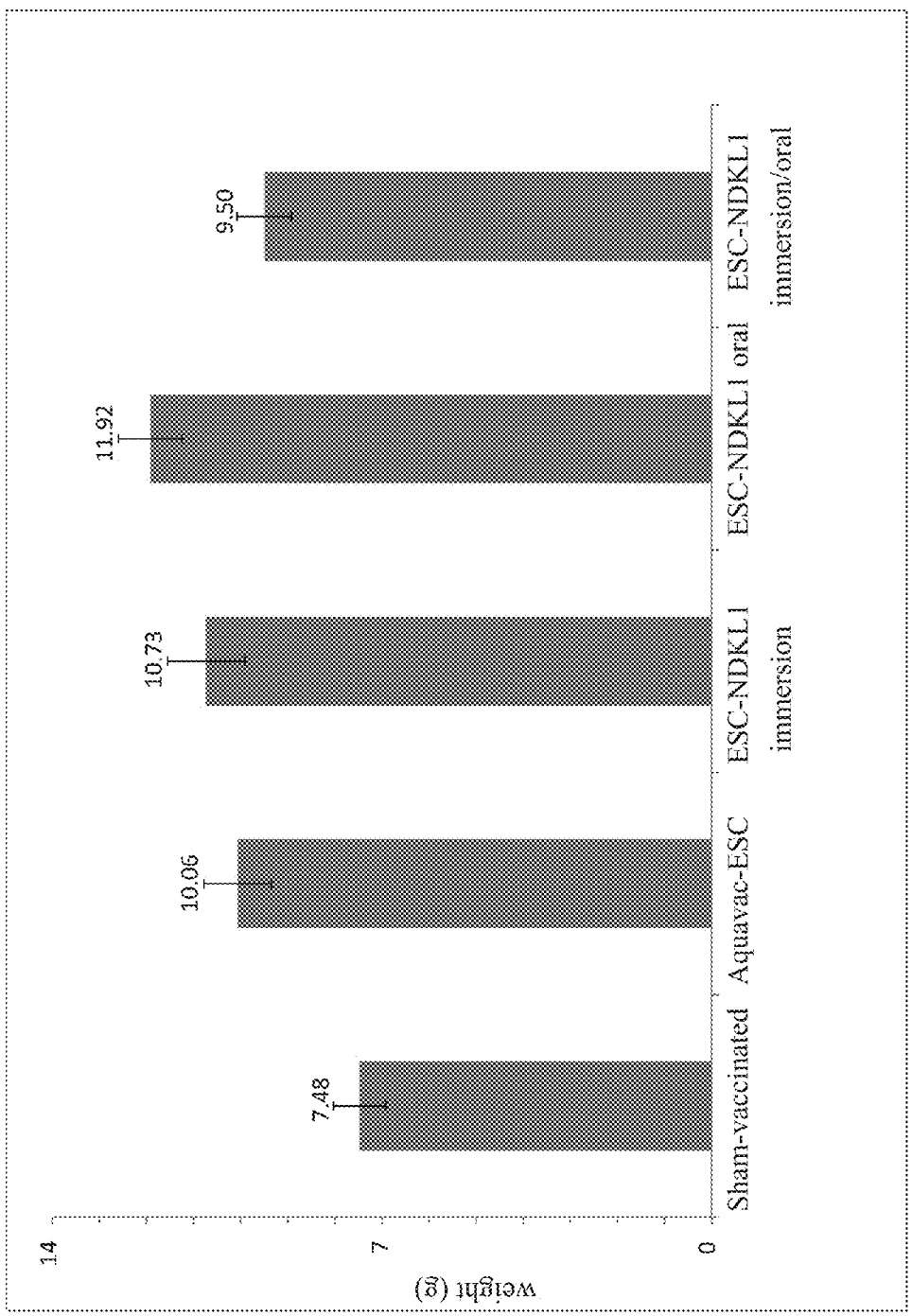
FIG. 9 is a bar graph showing the mean individual fish weight for thirty fish from each pen. This data represents the mean of four replicate pens in each pond.

The mean individual fish weights for 30 fish were 10.73, 11.92, 9.50, 10.06, and 7.48 g for immersion, oral, immersion-oral, AQUAVAC-ESC, and sham-vaccinated groups, respectively (see FIG. 9). Significantly higher individual fish weights were observed in the fish vaccinated with ESC-NDKL1 (ΔgcvPΔsdhCΔfrdA) by oral and immersion methods than the sham-vaccinated pond (p<0.0042 and 0.0513, respectively). Whereas, no significant differences were noted between ESC-NDKL1 immersion-oral vaccinated fish and AQUAVAC-ESC compared with sham-vaccinated pond.

Figure 10:
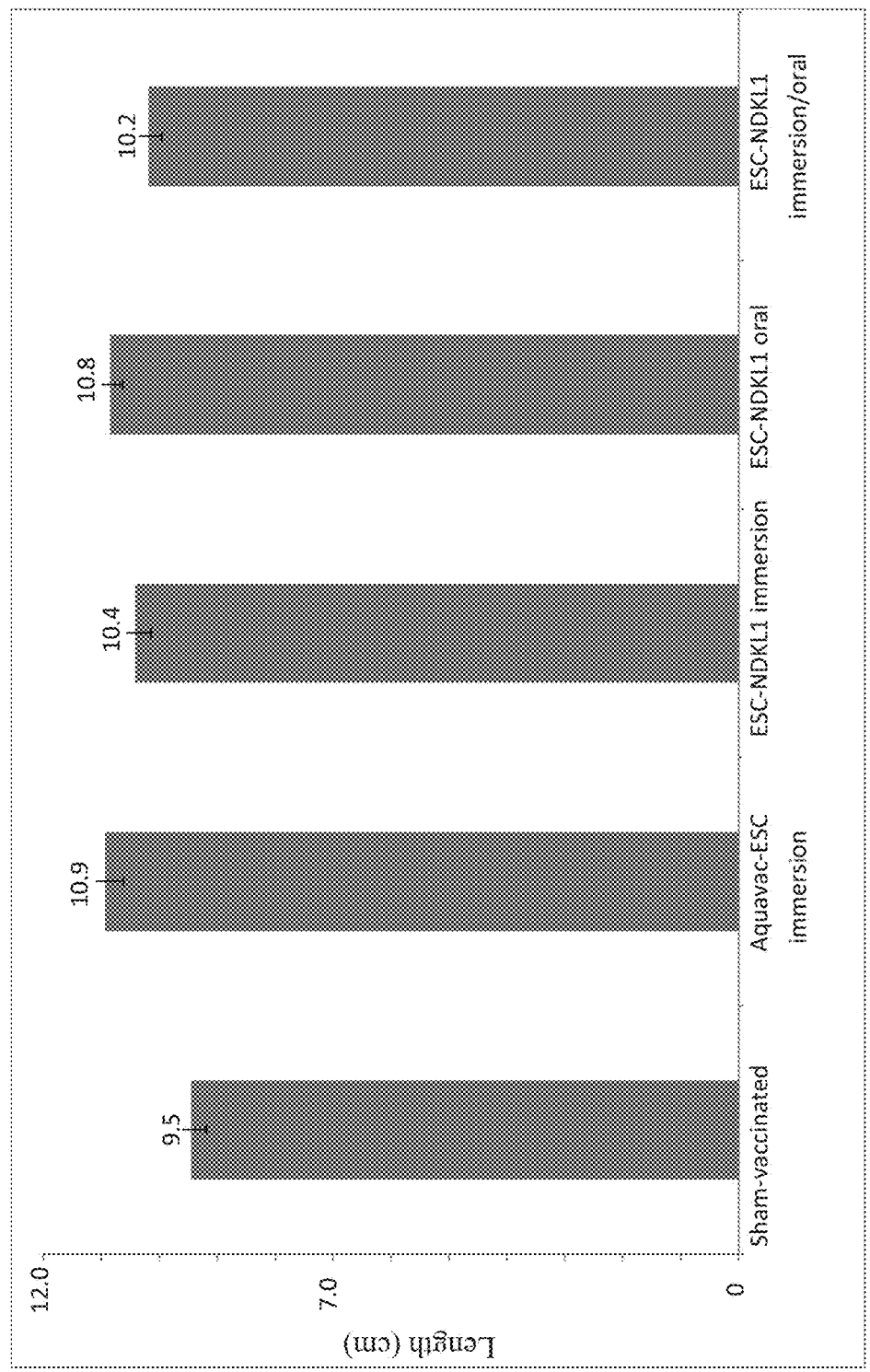
FIG. 10 is a bar graph showing the mean individual fish length for thirty fish from each pen. The data represents the mean of four replicate pens in each pond.

Mean individual fish lengths for 30 fish were 10.41, 10.84, 10.18, 10.91, and 9.45 cm for immersion, oral, immersion-oral, AQUAVAC-ESC, and sham-vaccinated groups, respectively. The differences in individual fish lengths were not significant between the vaccinated fish (ESC-NDKL1 (ΔgcvPΔsdhCΔfrdA) and AQUAVAC-ESC), and sham-vaccinated fish (see FIG. 10).

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference (as some are done so), to the extent each reference is at least partially not inconsistent with the disclosure in the present application (for example, a reference that is partially inconsistent is incorporated by reference except for the partially inconsistent portion of the reference).

We claim:

1. A composition for providing immunological protection from an enteric septicemia caused by *Edwardsiella ictaluri*, said composition comprises a live attenuated strain of *Edwardsiella ictaluri* comprising gene disrupting mutations in genes coding for three proteins in the group consisting of glycine cleavage system (gcvP), succinate dehydrogenase (sdhC), malate dehydrogenase (mdh), and fumarate reductase (frdA).

2. The composition of claim 1, wherein the three proteins having the gene disrupting mutations are glycine cleavage system (gcvP), succinate dehydrogenase (sdhC), and fumarate reductase (frdA).

3. The composition of claim 1, wherein the three proteins having the gene disrupting mutations are glycine cleavage system (gcvP), succinate dehydrogenase (sdhC), and malate dehydrogenase (mdh).

4. The composition of claim 1, wherein the gene disrupting mutations are in frame gene disrupting mutations.

5. A mutant bacterial strain of *Edwardsiella ictaluri* comprising gene disrupting mutations in genes coding for three proteins in the group consisting of glycine cleavage system (gcvP), succinate dehydrogenase (sdhC), malate dehydrogenase (mdh), and fumarate reductase (frdA).

6. The mutant bacterial strain of claim 5, wherein the three proteins having the gene disrupting mutations are glycine cleavage system (gcvP), succinate dehydrogenase (sdhC), and malate dehydrogenase (mdh).

7. The mutant bacterial strain of claim 5, wherein the three proteins having the gene disrupting mutations are glycine cleavage system (gcvP), succinate dehydrogenase (sdhC), and fumarate reductase (frdA).

8. The mutant bacterial strain of claim 5, wherein the gene disrupting mutations are in frame gene disrupting mutations.

9. A composition for providing immunological protection from an enteric disease caused by a pathogenic bacterial strain of *Enterobacteriaceae* comprising a live attenuated strain of the pathogenic bacterial strain of *Enterobacteriaceae* comprising gene disrupting mutations in genes coding for three proteins in the group consisting of glycine cleavage system (gcvP), succinate dehydrogenase (sdhC), malate dehydrogenase (mdh), and fumarate reductase (frdA).

10. The composition of claim 9, wherein the three proteins having the gene disrupting mutations are glycine cleavage system (gcvP), succinate dehydrogenase (sdhC), and malate dehydrogenase (mdh).

11. The composition of claim 9, wherein the three proteins having the gene disrupting mutations are glycine cleavage system (gcvP), succinate dehydrogenase (sdhC), and fumarate reductase (frdA).

12. The composition of claim 9, wherein the gene disrupting mutations are in frame gene disrupting mutations.

13. A method of providing immunological protection to an animal from an enteric disease caused by a pathogenic bacterial strain of *Enterobacteriaceae* in the animal comprising providing to the animal an effective amount of a live attenuated strain of the pathogenic bacterial strain of *Enterobacteriaceae* comprising gene disrupting mutations in genes coding for three proteins in the group consisting of glycine cleavage system (gcvP), succinate dehydrogenase (sdhC), malate dehydrogenase (mdh), and fumarate reductase (frdA).

14. The method of claim 13, wherein the three proteins having the gene disrupting mutations are glycine cleavage system (gcvP), succinate dehydrogenase (sdhC), and malate dehydrogenase (mdh).

15. The method of claim 13, wherein the three proteins having the gene disrupting mutations are glycine cleavage system (gcvP), succinate dehydrogenase (sdhC), and fumarate reductase (frdA).

16. The method of claim 13, wherein the gene disrupting mutations are in frame gene disrupting mutations.

17. A method of providing immunological protection to an animal from an enteric disease caused by a pathogenic bacterial strain of *Edwardsiella ictaluri* in the animal comprising providing to the animal an effective amount of a live attenuated strain of the pathogenic bacterial strain of *Edwardsiella ictaluri* comprising gene disrupting mutations in genes coding for three proteins in the group consisting of glycine cleavage system (gcvP), succinate dehydrogenase (sdhC), malate dehydrogenase (mdh), and fumarate reductase (frdA).

18. The method of claim 17, wherein the three proteins having the gene disrupting mutations are glycine cleavage system (gcvP), succinate dehydrogenase (sdhC), and malate dehydrogenase (mdh).

19. The method of claim 17, wherein the three proteins having the gene disrupting mutations are glycine cleavage system (gcvP), succinate dehydrogenase (sdhC), and fumarate reductase (frdA).

20. The method of claim 17, wherein the gene disrupting mutations are in frame gene disrupting mutations.

* * * * *